US006284789B1

(12) United States Patent
LaLonde et al.

(10) Patent No.: US 6,284,789 B1
(45) Date of Patent: Sep. 4, 2001

(54) FORMATION AND COMPOSITION OF NEW OPTICALLY ACTIVE COMPOUNDS

(75) Inventors: Robert T. LaLonde, Syracuse; Frank D. Ramdayal, New York; Mianji Zhang, Syracuse, all of NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/387,403

(22) Filed: Sep. 2, 1999

Related U.S. Application Data

(60) Provisional application No. 60/099,095, filed on Sep. 4, 1998.

(51) Int. Cl.$^7$ .................................................. A61K 31/35
(52) U.S. Cl. ...................... 514/451; 514/463; 514/468; 549/358; 549/432; 549/456; 549/457
(58) Field of Search .................................... 514/463, 468, 514/451; 549/432, 456, 457, 358

(56) References Cited

U.S. PATENT DOCUMENTS 4,609,644   9/1986   Nemec .

OTHER PUBLICATIONS

Kelleher, "Correlation of Tubulin–Binding and Antitumor Activities of Podophyllotoxin Analogs," *Cancer Treat. Rep.* 62(10):1443–1447 (1978).

Ayres et al., "Lignans. Part II. Reduction of Lactones of the Podophyllotoxin Group with Lithium Aluminum Hydride," *J. Chem. Society*, 5025–5030 (1962).

Rodrigo, "A Stereo–and Regiocontrolled Synthesis of Podophyllum Lignans," *J. Org. Chem.* 43:4538–4540 (1980).

Leiter et al., "Action on Sarcoma 37 of Compounds Related to Podophyllotoxin and to Alpha–And Beta–Peltatin," *Cancer Research*, 9:625–626 (1949).

Hartwell et al., "Relationship of the Steric Configuration of Podophyllotoxin and Related Lignans to Potency in Damaging Sarcoma," *J. Proc. Am. Assoc. Cancer Research*, 2:19 (1954).

Loike et al., "Structure–Activity Study of the Inhibition of Microtubule Assembly in Vitro by Podophyllotoxin and Its Congeners," *Cancer Research*, 38:2688–2693 (1978).

Brewer et al., "Conformational Analysis of Podophyllotoxin and Its Congeners. Structure–Activity Relationship in Microtubule Assembly," *J. Med. Chem.*, 22(3):215–221 (1979).

Tomioka et al., "Absolute Structure–Cytotoxic Activity Relationships of Steganacin Congeners and Analogues," *J. Med. Chem.*, 34:54–57 (1991).

*Primary Examiner*—Amelia Owens
(74) *Attorney, Agent, or Firm*—Nixon Peabody LLP

(57) ABSTRACT

The present invention is directed to tetrahydronaphthalene derivatives of α-conindendrin, β-conindendrin, sikkimotoxin, and podophyllotoxin having at least one methyleneoxy bridge wherein the oxygen atom extends to the benzhydrylic carbon atom.

13 Claims, 4 Drawing Sheets

Teniposide (4)    Etoposide (5)

2

β-Conidendrin

FORMATION AND COMPOSITION OF NEW OPTICALLY ACTIVE COMPOUNDS

This application claims the benefit of U.S. Provisional Patent Application Ser. No. 60/099,095, filed Sep. 4, 1998.

This invention was developed with government funding by the USDA-The Department of Agriculture Cooperative State Research Education and Extension Service, Grant No. 98CRMS06102. The U.S. Government may have certain rights.

FIELD OF THE INVENTION

The present invention relates to tetrahydronaphthalenes and to methods for treating cancer cells.

BACKGROUND OF THE INVENTION

α-Conidendrin (ACON), podophyllotoxin (PT), and sikkimotoxin (ST), respective structures 1–3 of FIG. 1, are naturally occurring tetrahydronaphthalene lignans. PT and ST are isolated from roots and rhizomes of the genus Podophyllum. Also, PT is a product of plant cell culture. PT is known to inhibit nucleoside transport in mammalian cells and assembly of microtubles and has antiviral and antitumor activity, among other biological activities. For example, PT binds to tubulin, thereby inhibiting the assembly of tubulin into microtubules. This, in turn, results in the arrest of cell division at the mitotic stage of the cell cycle. Kelleher, *Cancer Treat. Rep.*, 62: 1443 (1978)(Kelleher), reports a positive correlation between derivatives of PT and antineoplastic activity. In general, compounds which are strong inhibitors of microtubule assembly are believed to possess the strongest antitumor properties. However, because PT is highly toxic, it is not often used in medical applications.

Two semisynthetic derivatives of PT, teniposide and etoposide, respectfully shown as structures 4 and 5 in FIG. 2, are both effective in the treatment of a variety of leukemias and solid tumors. Although etoposide and teniposide are not inhibitors of microtubule assembly, they appear to exert their cytotoxic action through an interaction and inhibition of the enzyme tolpoisomerase II to cause increased single and double strand breaks in DNA. These and several other semisynthetic preparations from podophyllotoxin preserve the same carbo-oxygen, fused- and pendant-ring network possessed by podophyllotoxin. See U.S. Pat. No. 4,609,644 to Nemec.

Other derivative of podophyllotoxin have been produced. Ayers et al. *J. Chem. Soc.*, 5025–5030 (1962), report an oxabicyclooctane derivative produced by acid-catalyzed dehydration of podophyllol, a triol reduction product of PT. Rodrigo, *J. Org. Chem.*, 45(22): 4538–4540 (1980), reports an oxabicyclooctane prepared through acid catalyzed ether interchange in the course of a total synthesis of racemic podophyllotoxin. However, this intermediate was racemic as opposed to the optically active oxabicyclooctane derivatives of the present invention.

Structure-activity relationships studies indicate some structural features of PT and its derivatives influence their respective biological activity. Such structure-activity studies are reported by Letter et al., *Cancer Res.*, 9: 625 (1949); Hartwell et al., *J.Proc. Am. Assoc. Cancer Research*, 2:19 (1954); Kelleher; Loike et al., *Cancer Res.*, 38: 2688 (1978); Brewer et al., *J. Med. Chem.*, 22: 215 (1979); and Tomioka et al., *J. Med. Chem.*, 34: 54 (1991). Based upon these studies, the following general conclusions can be made: (a) a trans-fused relationship between C-9a and C-3a in ring D is important since the cis-fused derivatives exhibit greatly reduced or no biological activity, (b) the α-configuration of the pendant aryl ring (ring C) may be important for antitumor activity, but there is conflicting evidence on the importance of the configuration of the pendant aryl group, (c) the configuration of the hydroxyl group at C-9 has an effect on antitumor activity, but positioning of the hydroxyl group elsewhere in the molecule does not appear to have a marked effect on cytotoxic activity, (d) modification of the sugar moiety at C-9 in derivatives of PT can effect biological activity, and (e) conversion of the lactone ring of PT and deoxypodophyllotoxin (DPT) to a tetrahydrofuran ring diminishes inhibition of microtubule assembly by approximately 50%. Additionally, oxygenation at C-9 is required in etoposide and teniposide for the attachment of the glucopyranosyl unit.

ACON is an aryltetralin lignan found in sulfite waste liquor from pulping of the western hemlock. It is a white crystalline solid and occurs in two crystalline forms, one melting at approximately 255–256° C. and the other melting at 238° C. Although structurally similar to PT. it lacks the pendant aryl ring configuration present in many such cytotoxic, tetrahydronaphthalene lignans. Refluxing ACON with sodium methoxide in methanol results in the epimerization of the C-9a chiral center to give β-conidendrin (BCON), shown in FIG. 3. BCON and picropodophyllotoxin are stereoisomers of ACON and podophyllotoxin, respectively, As an antitumor agent, ACON, BCON, and picropodophyllotoxin are biologically inactive.

A large number of derivatives of ACON and BCON have been synthesized. Most of these derivatives involve protection of —OH groups on rings A and D. As shown in FIG. 4, synthesized derivatives of ACON and BCON protect the —OH groups on rings A and D as a methoxy (19) and (23). Other synthesized derivatives of ACON protect the —OH groups on rings A and D as acetoxy, benzoyl, and toluenesulphonyl groups. Similarly, other synthesized derivatives of BCON protect the —OH groups on rings A and D as acetoxy and toluenesulfonyl groups. The tetraacetyl and terabenzoyl derivatives of α-conidendrol have also been synthesized. However, there is no known report on the selective protection of the —OH groups on rings A and D.

As shown in the reaction sequences of FIG. 4, other derivatives of ACON and BCON have been synthesized from dimethyl-α-conidendrin (19) and dimethl-β-conidendryn (23). These derivatives are dimethyl-α-conidendryl alcohol (30), dimethyl-β-conidendryl alcohol (31), dimethylanhydro-α-conidendryl alcohol (32), and dimethylanhydro-β-conidendryl alcohol (33).

As can be seen, there are problems associated with the use of various naturally occurring tetrahydronaphthalene lignans as molecular source materials for cytotoxic agents. One such problem is the presence of an enolizable lactone; the second is an initial stereochemical configuration of the pendant aryl group inconsistent with achieving high cytotoxicity.

In view of the serious health effects of cancer, the need continues for compounds which exhibit cytotoxic effects on cancer cells. Further, there is a need for tetrahydronaphthalene lignans which can be utilized as a molecular source material for cytotoxic agents. Still, there is a need for derivative tetrahydronaphthalenes which possess a stereochemical configuration which provides high cytotoxicit. The present invention is directed to overcoming these deficiencies in the art.

SUMMARY OF THE INVENTION

The present invention relates to single and double methyleneoxy bridged compounds having the following formula:

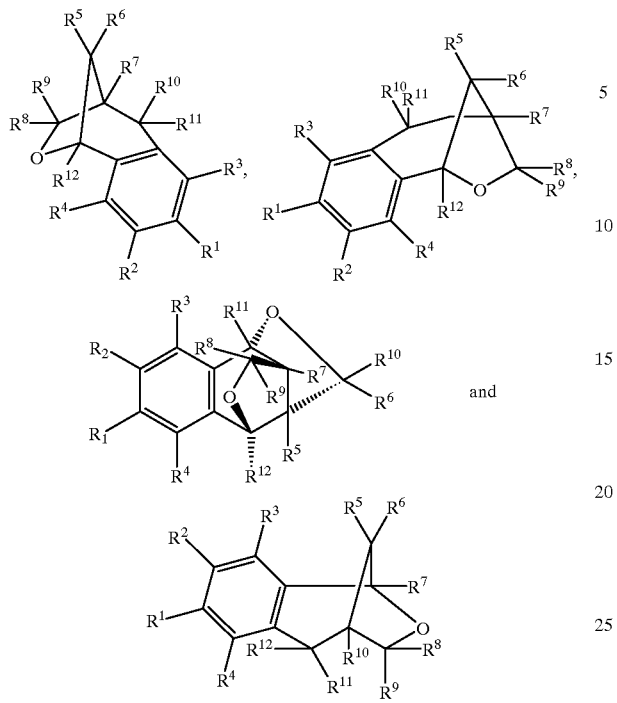

wherein
- $R^1$ and $R^2$ together with the atoms to which they are bonded form a substituted or unsubstituted homocyclic or heterocyclic saturated, unsaturated, or aromatic ring, or $R^1$ and $R^2$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^a$, where $R^a$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;
- $R^3$, $R^4$, $R^7$, $R^{10}$, and $R^{11}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carboxylic acid amide group; and a group having the formula —OC(O)$R^b$, where $R^b$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;
- $R^8$ and $R^9$ together with the atoms to which they are bonded form a substituted or unsubstituted, homocyclic or heterocyclic, saturated, unsaturated, or aromatic ring, or $R^8$ and $R^9$ are independently selected from the group consisting of hydrogen; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^c$, where $R^c$ is selected from the group consisting of substituted or unsubstituted alkyl; substituted or unsubstituted aralkyl; substituted or unsubstituted aryl; a substituted or unsubstituted saturated, unsaturated or aromatic heterocyclic group;
- $R^5$ and $R^6$ together with the atoms to which they are bonded form a substituted or unsubstituted, homocyclic or heterocyclic, saturated, unsaturated, or aromatic ring, or $R^5$ and $R^6$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^d$ where $R^d$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;
- $R^{12}$ is a group having the formula:

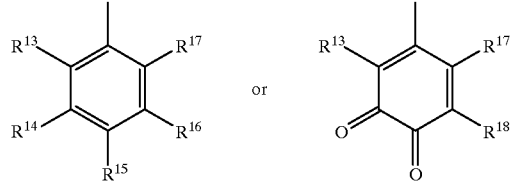

- $R^{13}$, $R^{14}$, $R^{17}$, and $R^{18}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O) $R^e$, where $R^e$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^{15}$ and $R^{16}$ are independently selected from the group consisting of hydroxy; substituted or unsubstituted alkoxy; substituted or unsubstituted arylxoxy; and substituted or unsubstituted aralkoxy; or $R^{15}$ and $R^{16}$, together, have the formula —O—Z—O— where Z is a substituted or unsubstituted alkylene moiety.

The present invention also provides a method of treating cancer cells comprising contacting cancer cells with the compounds having the above formulae under conditions effective to kill the cancer cells. Treatment comprises administering to the patient, whether plant or animal, a therapeutically effective amount of such compounds.

Further, the present invention relates to a method for making the above bridged tetrahydronaphthalene derivatives comprising providing either α-conindendrin, β-conindendrin, sikkimotoxin, podophyllotoxin, or derivatives thereof and introducing an oxidizing agent, e.g. 2,3-dichloro-5,6-dicyano-1,4-benzoquinone or copper sulfate/potassium peroxydisulfate, to the α-conindendrin, β-conindendrin, sikkimotoxin, podophyllotoxin, or substituted derivatives thereof under conditions effective to form the methyleneoxy bridged tetrahydronaphthalene.

DETAILED DESCRIPTION OF THE INVENTION

Figure 1:
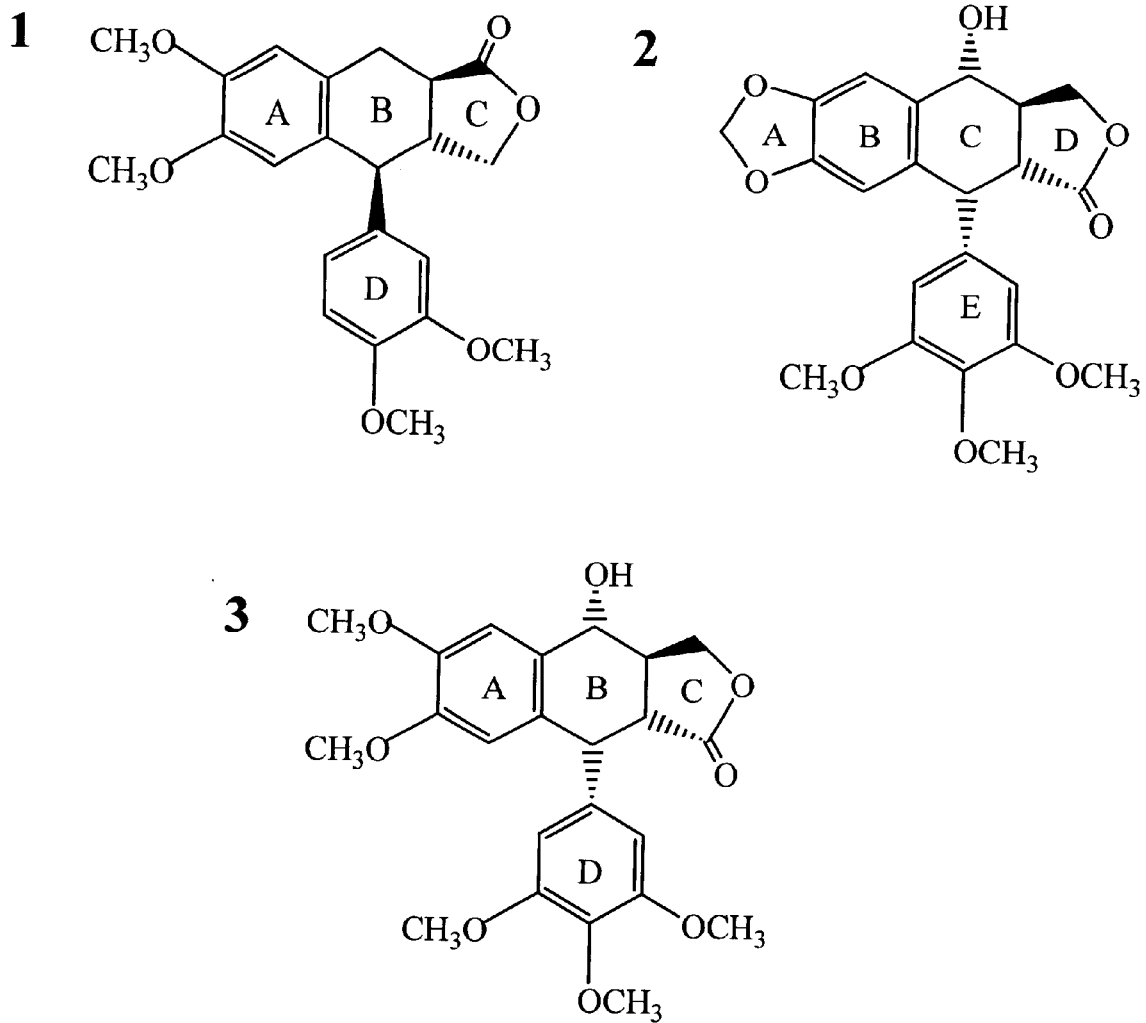
FIG. 1 is a schematic showing the chemical structures of α-conidendrin, podophyllotoxin, and sikkimotoxin.
Figure 2:
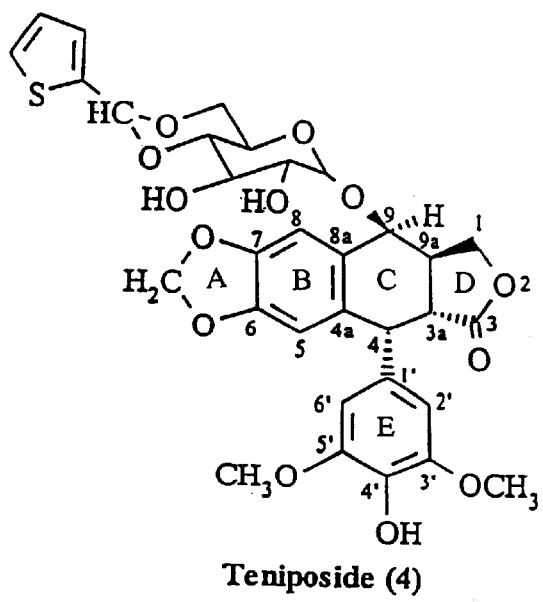
FIG. 2 is a schematic showing the chemical structures of teniposide and etoposide.
Figure 2:
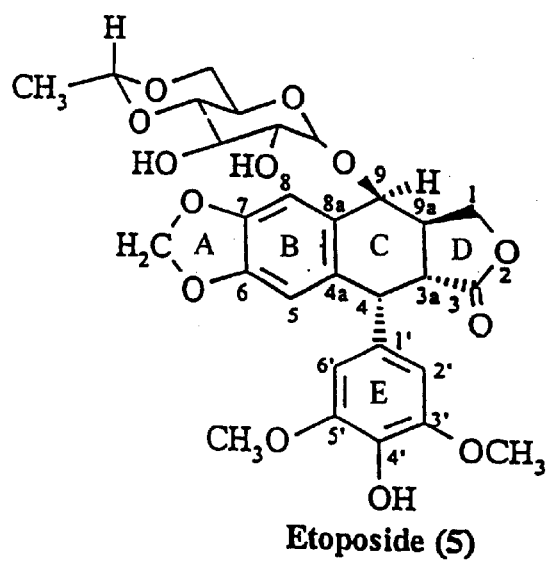
Figure 3:
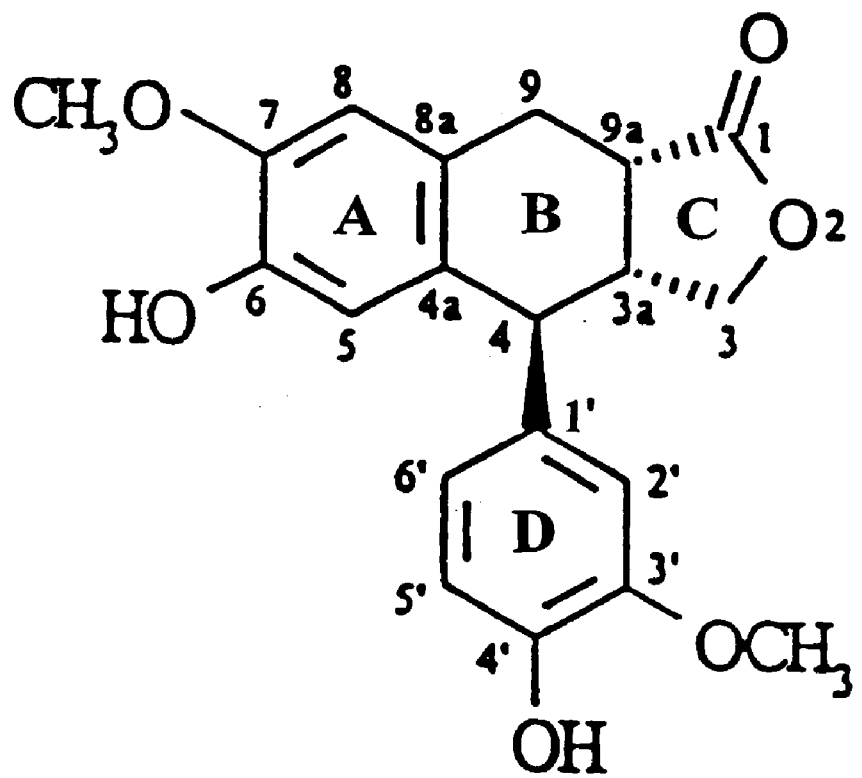
FIG. 3 is a schematic showing the chemical structure of β-conidendrin.
Figure 4:
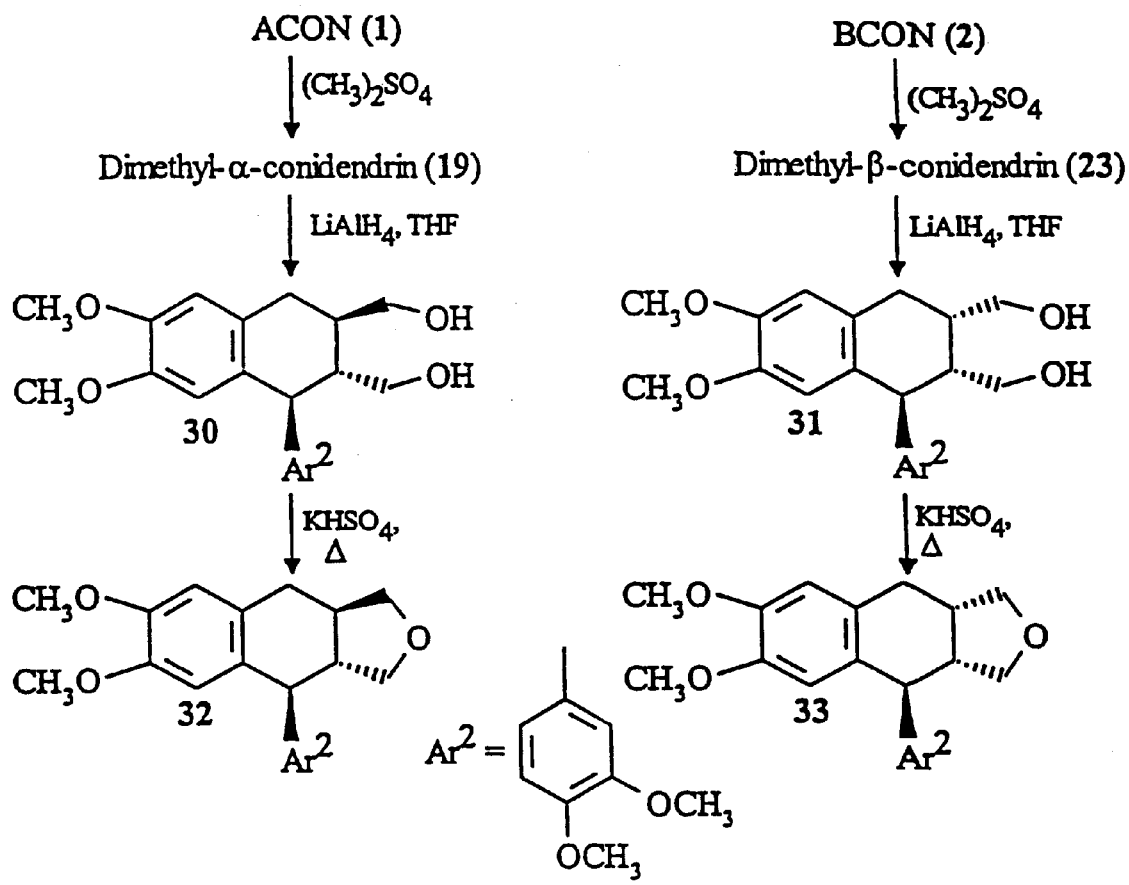
FIG. 4 is a schematic showing the reaction steps to produce dimethyl-α-conidendryl alcohol, dimethyl-β-conidendryl alcohol, dimethylanhydro-α-conidendryl alcohol, and dimethylanhydro-β-conidendryl alcohol.

The present invention relates to methyleneoxy bridged tetrahydronaphthalenes and to methods for killing or preventing the reproduction of cancer cells using these tetrahydronaphthalenes. One aspect of the present invention relates to methyleneoxy bridged compound having the formula:

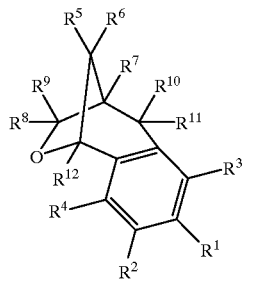

$R^1$ and $R^2$ together with the atoms to which they are bonded form a substituted or unsubstituted homocyclic or heterocyclic saturated, unsaturated, or aromatic ring. Alternatively $R^1$ and $R^2$ are independently selected from the group consisting of hydrogen; hydroxy; substituted or Lisubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^a$, where $R^a$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group.

$R^3$, $R^4$, and $R^7$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^b$ where $R^b$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group.

$R^5$ and $R^6$ together with the atoms to which they are bonded form a substituted or unsubstituted, homocyclic or heterocyclic, saturated, unsaturated, or aromatic ring. Alternatively, $R^5$ and $R^6$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^c$, where $R^c$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^8$ and $R^9$ together with the atoms to which they are bonded form a substituted or unsubstituted, homocyclic or heterocyclic, saturated, unsaturated, or aromatic ring. Alternatively, $R^8$ and $R^9$ are independently selected from the group consisting of hydrogen; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)R$^d$, where R$^d$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group.

R$^{10}$ and R$^{11}$ together with the atoms to which they are bonded form a substituted or unsubstituted, homocyclic or heterocyclic, saturated, unsaturated, or aromatic ring. Alternatively, R$^{10}$ and R$^{11}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)R$^e$ where R$^e$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group.

R$^{12}$ is a group having the formula:

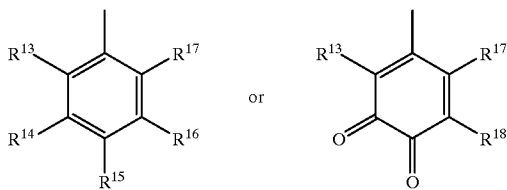

R$^{13}$, R$^{14}$, R$^{17}$, and R$^{18}$ are independently selected from the group consisting of hydrogen; hydroxy; substituted or unsubstituted alkyl; substituted or unsubstituted aralkyl; substituted or unsubstituted aryl; a substituted or unsubstituted saturated unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)R$^f$, where R$^f$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group.

R$^{15}$ and R$^{16}$ are independently selected from the group consisting of hydroxy; substituted or unsubstituted alkoxy; substituted or unsubstituted arylxoxy; and substituted or unsubstituted aralkoxy; or R$^{15}$ and R$^{16}$, together, have the formula —O—Z—O— where Z is a substituted or unsubstituted alkylene moiety. This compound can be derived from α-conindendrin, sikkimotoxin, podophyllotoxin, and substituted derivatives thereof.

Another aspect of the present invention relates to a methyleneoxy bridged compound having the formula:

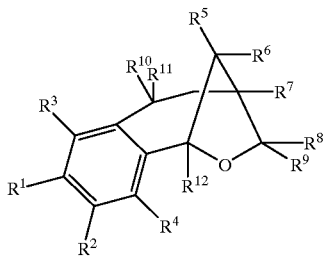

R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ have the same definitions as described above. This compound can be derived from β-conindendrin and substituted derivatives thereof.

Still, another aspect of the present invention relates to a methyleneoxy bridged compound having the formula:

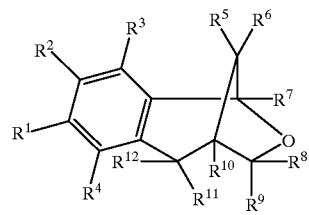

R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ have the same definitions as described above, except R$^7$ excludes hydroxy. This compound can be derived from β-conindendrin and derivatives thereof.

Yet, another aspect of the present invention relates to a compound having two methyleneoxy bridges in a dioxatricyclodecane and has the following formula:

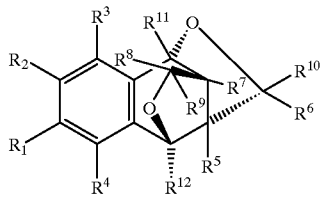

R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ have the same definitions as described above. Compounds possessing a single methyleneoxy bridge in an oxabicyclooctane, and, in addition, possessing a hydroxymethylene group attached in the positions and stereochemical configurations shown in structures I and II, are oxidized by the appropriate oxidizing agent and conditions to a molecule incorporating the two methyleneoxy bridges as exemplified by this dioxatricyclodecane. Oxidizing agents include quinones, for example, 2,3-dichloro-5,6-dicyanobenzoquinone (DDQ), and copper sulfate/potassium peroxydisulfate.

Preferred compounds are those wherein R$^1$ and R$^2$ are alkoxy, aryloxy, alkenyldioxy, aralkenyldioxy, cycloalkenyldioxy, where the aromatic ring may optionally be substituted, preferably by one or more of hydroxy, alkyl, alkoxy, nitro, amine, phenylalkyl, or halogen radicals. Most preferred, R$^1$ and R$^2$ are methoxy or where R$^1$ is connected to R$^2$ as in a methylenedioxy group. Further, the preferred compounds, in combination with the preferred substitutents of $R^1$ and $R^2$ above, include those where $R^{14}$, $R^{15}$, and $R^{16}$ are all hydrogens, a combination of two hydrogens and one hydroxy, alkoxy, or aryloxy group, a combination of one hydrogen and two hydroxy, alkoxy, arlyoxy, alkenyldioxy, aralkenyldioxy, or cycloalkenyldioxy, where the aromatic ring may optionally be substituted preferably by one or more hydroxy, alkyl, alkoxy, nitro, or halogen radicals. Alternatively, the preferred compounds include those where $R^{14}$, $R^{15}$, and $R^{16}$ are all hydroxy, alkoxy, aralkyloxy, or a combination of any one moiety with different moieties including alkenyldioxy, aralkenyldioxy, or cycloalkenyldioxy, where the aromatic ring may optionally be substituted by one or more hydroxy, alkyl, alkoxy, nitro, or halogen radicals. Most preferred, $R^{14}$, $R^{15}$, and $R^{16}$ are methoxy groups in combination with the preferred substitutents of $R^1$ and $R^2$. This compound can be derived from α-conindendrin, sikkimotoxin, podophyllotoxin, and derivatives thereof.

Compounds of the present invention are synthesized by reacting an oxidizing agent with a tetrahydronaphthalene derivative diol under conditions effective to form the methyleneoxy bridged tetrahydronaphthalene. Preparation of such diols is described in Gensler et al., *J. Med. Chem.*, 20(5): 635–644 (1977), which is incorporated herein by reference. As indicated above the preferred diols are α-conindendrin, β-conindendrin, sikkimotoxin, podophyllotoxin, and derivative thereof. Oxidizing agents include quinones, for example, 2,3-dichloro-5,6-dicyanobenzoquinone (DDQ), and copper sulfate/potassium peroxydisulfate.

Three structural classes of methyleneoxy-bridged derivatives can result. In two of the three, single methyleneoxy bridging is directed to two different carbon atoms of the precursor diol, resulting in derivatives having the following general structures:

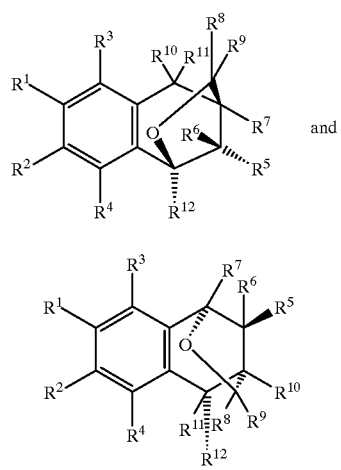

When $R^1$ and $R^2$ are alkoxy, $R^{12}$ is an aryl, and $R^{15}$ and $R^{16}$ are an alkoxy, the derivative has the structure of compound I. Alternatively, when $R^1$ is alkoxy, $R^2$ is hydroxy, $R^{12}$ is an aryl, $R^{15}$ is a hydroxy, and $R^{16}$ is an alkoxy, for example, a methoxy, the derivative has the structure of compound II.

Compounds possessing a single methyleneoxy bridge in an oxabicyclooctane, and, in addition, possessing a hydroxymethylene group attached in the positions and stereochemical configurations shown in structures I and II, are oxidized by the appropriate oxidizing agent and conditions to a molecule incorporating the two methyleneoxy bridges as exemplified by this dioxatricyclodecane. Oxidizing agents include quinones, for example, 2,3-dichloro-5,6-dicyanobenzoquinone (DDQ), and copper sulfate/potassium peroxydisulfate.

Generally, 1.0–3.0 equivalents by mole of oxidizing agent for each equivalent of diol are employed. For DDQ, a preferred range of oxidizing agent is 1.0–1.2, with 1.0–1.1 equivalents being the most preferred ranges. For copper sulfate/potassium peroxydisulfate, a preferred range of oxidizing agent is 2.0–2.4, with 2.0–2.2 equivalents being the most preferred ranges. The reaction may be carried out in suspension or in an appropriate solvent or aqueous-solvent solution. Reactions are conducted at a temperature between about 22° C. and 45° C. For DDQ, the reactions are conducted at ambient temperature, such as between about 22° C. and 80° C. Reaction times can vary from a few minutes to several hours.

On completion of the reaction, the desired products may be isolated from the reaction mixture by extraction with a solvent, ethyl acetate being preferred. The product may be further purified by any suitable purification method, with chromatography and crystallization being preferred methods. Oxabicyclooctane and dioxatricyclodecane derivatives of the present invention are active in several cell lines of a sixty cell line panel, which includes leukemia, melanoma, non-small cell lung, colon, CNS, ovarian, renal, prostate, and breast cancers. Testing results are reported below in Example 16.

As indicated above, another aspect of the present invention is directed to therapeutically treating a subject suffering from cancer. A method of killing cancer cells comprises contacting cancer cells with a compound of the present invention under conditions effective to kill the cancer cells. Treatment comprises administering to the patient, whether plant or animal, an effective amount of a compound of the present invention.

It will be appreciated that the actual preferred amount of compound of the present invention used will vary according to the particular compound, the particular composition formulated, and the mode of application. Many factors that modify the action will be taken into account by those skilled in the art; e.g., body weight, sex, diet, time of administration, route of administration, rate of excretion, condition of the host, drug combinations, reaction sensitivities and severities, type of tumor or cancer and associated cancer cells, and severity of cancer development within the host. Administration can be carried out continuously or periodically within the maximum tolerated dose. Optimal application rates for a given set of conditions can be ascertained by those skilled in the art using conventional dosage administration tests in view of the above guidelines.

Another aspect of the present invention is the selective oxygenation of C-9 of conidendrin and derivatives thereof, and the inversion of the stereochemical C-4 chiral center of derivatives of conidendrin. Table 1 summarizes the results of the reaction of substituted tetralins with 2,3-dichloro-5,6-dicyano-1,4-benzoquinone (DDQ). Entries h, i, and j show the results of oxidation of 6,7-disubstituted tetralins with DDQ in aqueous dioxane. With entry h, benzylic oxygenation occurred para to the —OH group and not the —OCH$_3$ group. Likewise in entry i, oxygenation of the benzylic position of 6-acetoxy-6-methoxytetralin occurred para to the —OCH$_3$ group and not the acetoxy group. Hence, the relative directing preference of the OH, OCH$_3$, and OCOCH$_3$ groups for para bencylic oxygenation by DDQ is —OH>—OCH$_3$>—OCOCH$_3$.

TABLE 1

Summary of reactions of DDQ with model tetralin compounds.

| Entry | Substrate | Equiv.[a] of DDQ | Solvent | Product |
|---|---|---|---|---|
| a | 6-acetoxy tetralin (93) | 2 | aqueous dioxane | No reaction |
| b | 6-hydroxy tetralin (76) | 2 | aqueous dioxane | 6-hydroxy-1-tetralone (77, 75%) |
| c | 6-hydroxy tetralin (76) | 2 | MeOH | 6-hydroxy-1-tetralone (77, 72%) |
| d | 6-hydroxy tetralin (76) | 1 | acetic acid | coupled dimer (78, 58%) |
| e | 6-methoxy tetralin (79) | 2 | aqueous dioxane | 6-methoxy-1-tetralone (80, 72%) + 2-methoxynaphthalene (81, 15%) |
| f | 6-methoxy tetralin (79) | 2 | MeOH | 6-methoxy-1-tetralone (80, 69%) |
| g | 6-methoxy tetralin (79) | 1 | acetic acid | 1-acetoxy-6-methoxytetralin (82, 71%) + 2-methoxynaphthalene (83, 8%) |
| h | 6-methoxy-7-hydroxy tetralin (84) | 2 | aqueous dioxane | 6-methoxy-7-hydroxy-1-tetralone (85, 71%) |
| i | 6-methoxy-7-acetoxy tetralin (86) | 2 | aqueous dioxane | 7-acetoxy-6-methoxy-1-tetralone (87, 62%) + 3-methoxy-2-acetoxynaphthalene (88, 23%) |

TABLE 1-continued

Summary of reactions of DDQ with model tetralin compounds.

| Entry | Substrate | Equiv.[a] of DDQ | Solvent | Product |
|---|---|---|---|---|
| j | 6,7-dimethoxytetralin (90) | 2 | aqueous dioxane | 6,7-dimethoxy-1-tetralone (91, 68%) + 2,3-dimethoxynaphthalene (92, 20%) |

[a]Equiv. - equivalent.

It will be appreciated that the actual preferred amount of compound of the present invention used will vary according to the particular compound, the particular composition formulated, and the mode of application. Many factors that modify the action will be taken into account by those skilled in the art; e.g., body weight, sex. diet, time of administration, route of administration, rate of excretion, condition of the host, drug combinations, reaction sensitivities and severities, type of tumor or cancer and associated cancer cells, and severity of cancer development within the host. Administration can be carried out continuously or periodically within the maximum tolerated dose. Optimal application rates for a given set of conditions can be ascertained by those skilled in the art using conventional dosage administration tests in view of the above guidelines.

Another aspect of the present invention is the selective oxgenation of C-9 of conidendrin and derivatives thereof, and the inversion of the stereochemical C-4 chiral center of derivatives of conidendrin. Table 1 summarizes the results of the reaction of substituted tetralins with 2,3-dichloro-5,6-dicyano-1,4-benzoquinone (DDQ). Entries h, i, and j show the results of oxidation of 6,7-disubstituted tetralins with DDQ in aqueous dioxane. With entry h, benzylic oxygenation occurred para to the —OH group and not the —OCH$_3$ group. Likewise in entry i, oxygenation of the benzylic position of 6-acetoxy-6-methoxytetralin occurred para to the —OCH$_3$ group and not the acetoxy group. Hence, the relative directing preference of the OH, OCH$_3$, and OCOCH$_3$ groups for para bencylic oxygenation by DDQ is —OH>—OCH$_3$>—OCOCH$_3$.

Also evident from the results in Table 1, replacement of the —OH group with a —OCH$_3$ or a —OCOCH$_3$ group increased the relative amounts of product in which the fused cyclohexane ring of the tetralin compounds was dehydrogenated.

From the studies of benzylic oxygenation of model tetralin compounds with DDQ as shown in Table 1, it can be concluded that: (a) benzylic oxygenation with DDQ occurs efficiently in aqueous dioxane and with a slightly lesser efficiency in methanol, (b) the relative directing preference for para benzylic oxygenation by DDQ is —OH>—OCH$_3$>—OCOCH$_3$, and (c) replacement of the —OH group para to the benzylic position with —OCH$_3$ or —OCOCH$_3$, appears to result in increased dehydrogenation of the fused cyclohexane ring.

Table 2 shows a summary of the results of the reaction of DDQ with ACON, BCON, and their derivatives. Attempts to oxygenate C-9 of ACON with DDQ in aqueous dioxane and dimemthl-α-conidendrin (19) with DDQ in acetic acid resulted in dehydrogyenation of ring B (entries a and b respectively). Attempts to oxygenate C-9 of dimethylanhydro-β-conidendryl alcohol (33) and 4'-O-methylanhydro-α-conidendryl alcohol (135) with DDQ in aqueous dioxane resulted in dehydrogenation of ring B and the oxidation of the tetrahydrofuran ring to a lactone ring (entries c and d, respectively).

TABLE 2
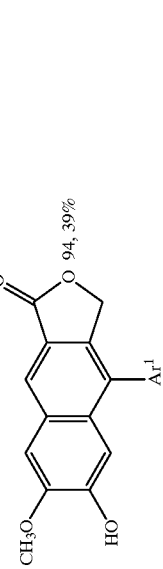

TABLE 2-continued

Summary of reactions of derivatives of ACON, BCON and PT, with DDQ.[a]

| Entry | Substrate | Equiv. of DDQ | Solvent | Product |
|---|---|---|---|---|
| f | 95 | 1.1 | dioxane | 96, 59%; 98, 14% |
| g | 97 | 1.1 | dioxane | 99, 63%; 110, 2% |
| h | 30 | 1.1 | $CH_2Cl_2$ | 109, 48%; 107, 1% |

TABLE 2-continued

Summary of reactions of derivatives of ACON, BCON and PT, with DDQ.[a]

| Entry | Substrate | Equiv. of DDQ | Solvent | Product |
|---|---|---|---|---|
| i | 31 | 1.1 | $CH_2Cl_2$ | 101, 70% + 102, 2% |
| j | 141 | 1.1 | $CH_2Cl_2$ | 142, 40% |

[a] Ar¹ =, Ar² =, Ar³ =

TABLE 2-continued
Summary of reactions of derivatives of ACON, BCON and PT, with DDQ.[a]
| Entry | Substrate | Equiv. of DDQ | Solvent | Product |
|---|---|---|---|---|
| | 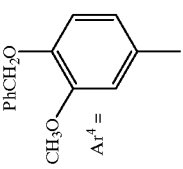 | | | |

There are two benzylic carbons (C-9 and C-4) in ACON, BCON and their derivatives. H-4 and one of the C-9 protons are almost orthogonal to the plane of ring A, and hence are in a stereochernically favorable conformation for hydride abstraction by DDQ. However. when dimethylanhydro-α-conidendryl alcohol (32) was reacted with DDQ in aqueous THF at −77° C., the major product produced only has the C-4—C-3a bond dehydrogenated to give compound 116 (see entry e). Hence, it appears that in the lactone and tetrahydroftiran derivatives of ACON and BCON, the C-4—C-3a bond is initially dehydrogenated. Therefore, initial hydride abstraction by DDQ takes place at the C-4 position during dehydrogenation to gie a quinone methide or a carbocation, depending on the structure of the substrate. Moreover, the preferred reaction pathway upon abstraction of the hydride ion from either C-4 or C-9 is dehydrogenation rather than substitution. This implies that the activation energy for nucleophilic attack by water on a carbocation at C-4 or C-9 is higher than the activation energy for dehydrouenation of a carbocation at C-4 or C-9.

Single bridged derivatives of the present invention can be synthesized from α- and β-conidendrin and their derivatives, sikkimotoxin at its derivatives, and podophyllotoxin derivatives. For example, dimethyl-α-conidendryl alcohol, dimethyl-β-conidendryl alcohol and deoxypodophyllol respectively, in reactions with DDQ produced compounds in accordance with the present invention (see Table 2, entries h, i, and j, respectively). Thus, for dimethyl-α-conidendryl alcohol, dimethyl-β-conidendryl alcohol and deoxypodophyllol, hydride abstraction by DDQ from C-4 is preferred over hydride abstraction from C-9. This result contrasts with what occurred with α- and β-conidendryl alcohols, where hydride abstraction by DDQ at C-9 was preferred over hydride abstraction at C-4.

EXAMPLES

Compounds according to the present invention were synthesized as described in detail below with reference to the following reactions schemes:

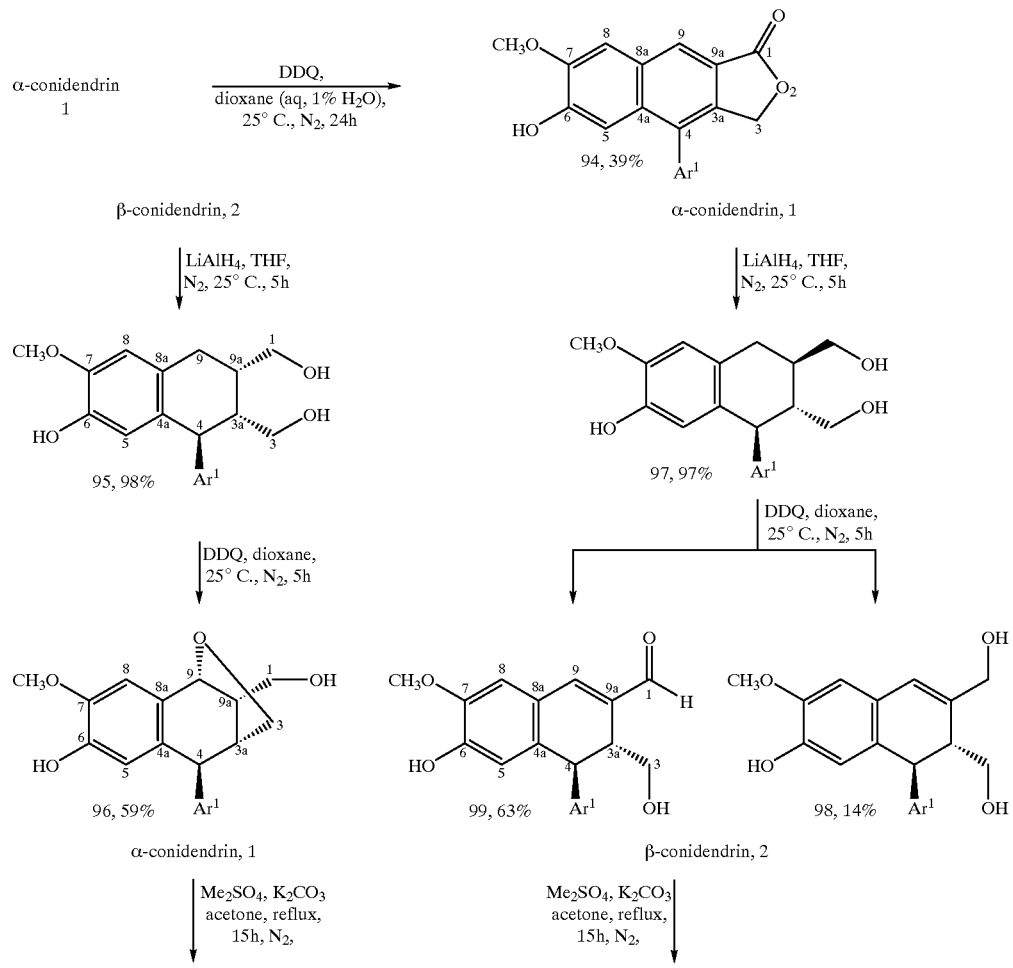

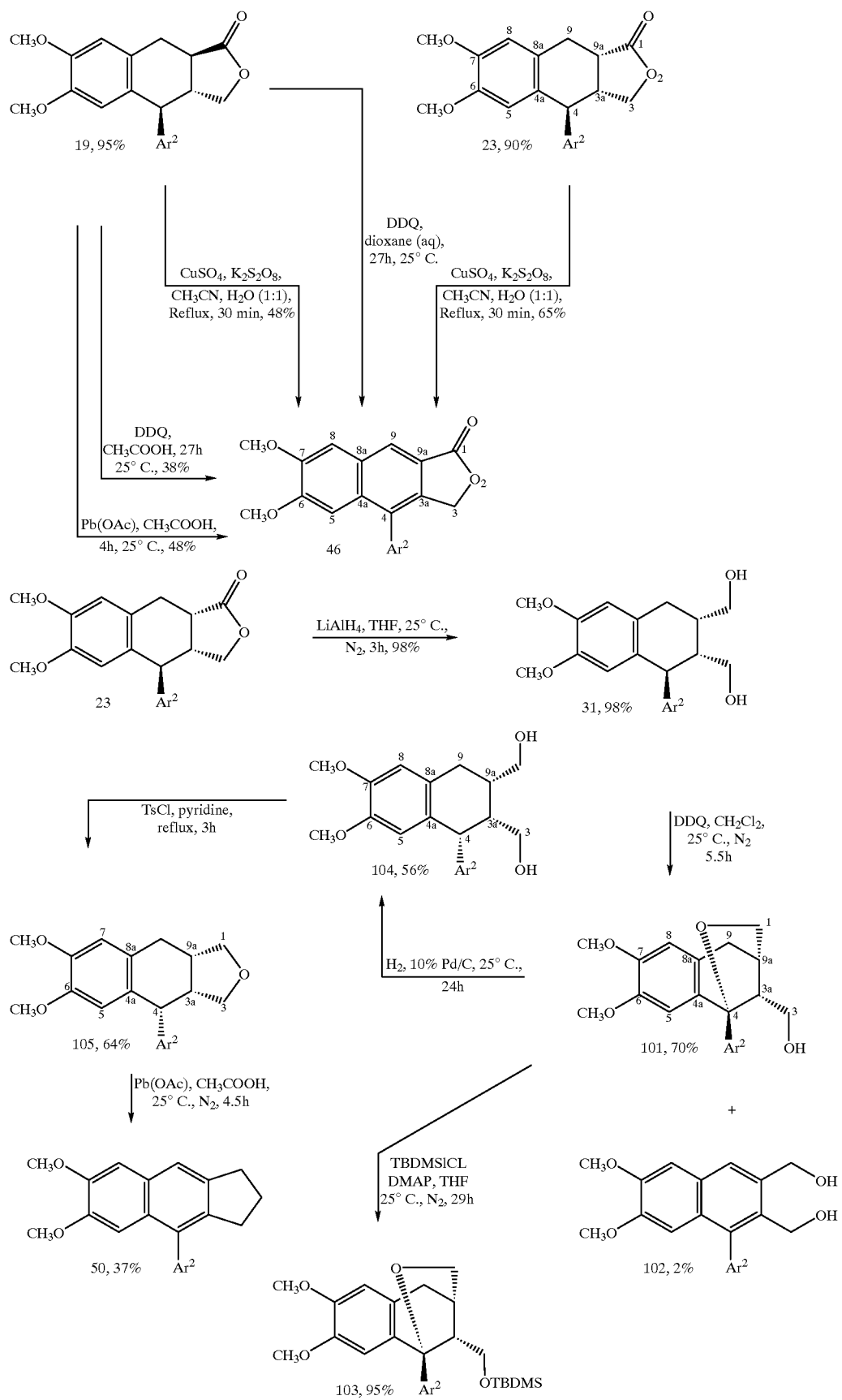

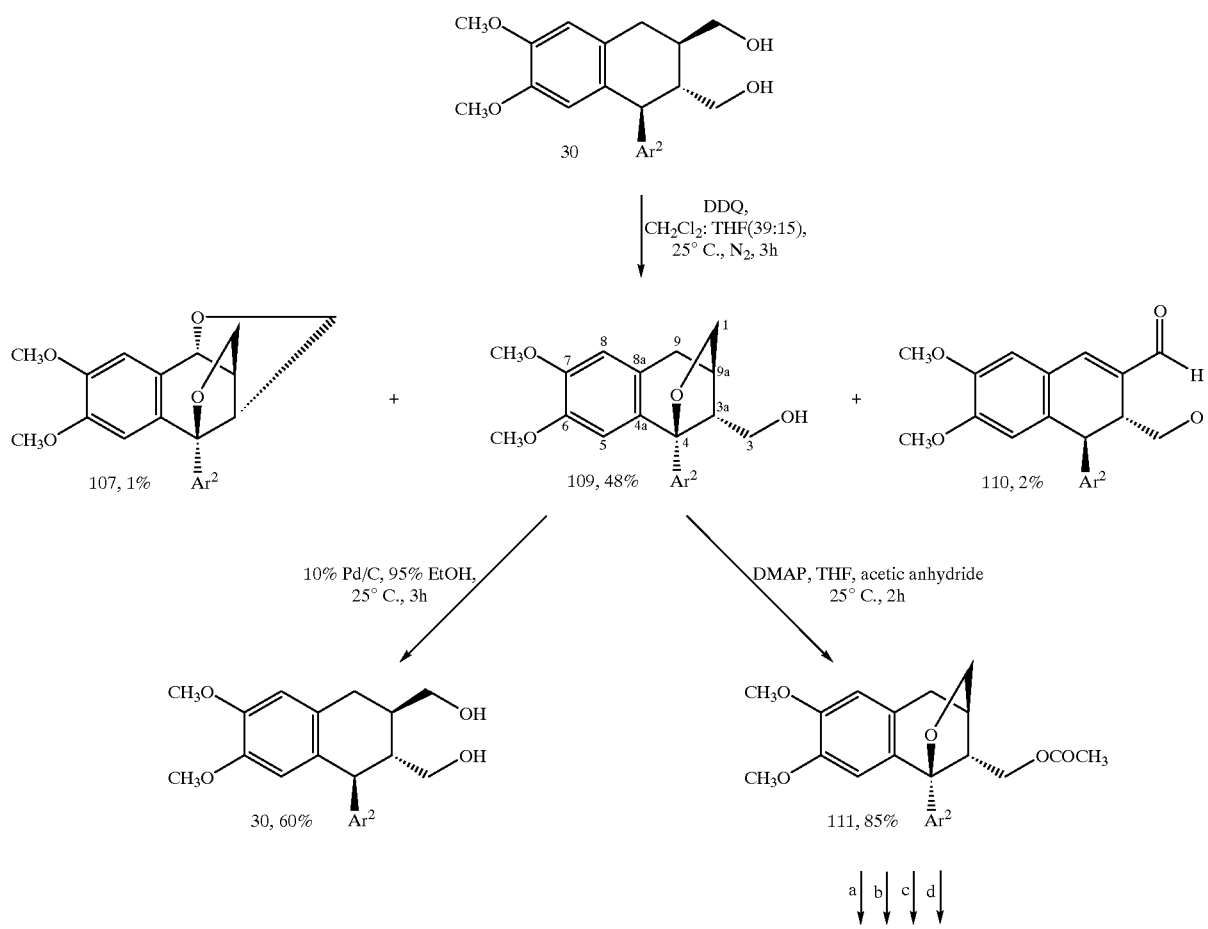
(a) Pb(OAc)$_4$, CH$_3$COOH, N$_2$, 25° C., 5h
(b) Pb(OAc)$_4$, CH$_3$COOH, N$_2$, 75° C., 3h
(c) PCC, tert-butylhydroperoxide, 25° C., 22h
(d) DDQ, MeOH, 25° C., N$_2$, 24h
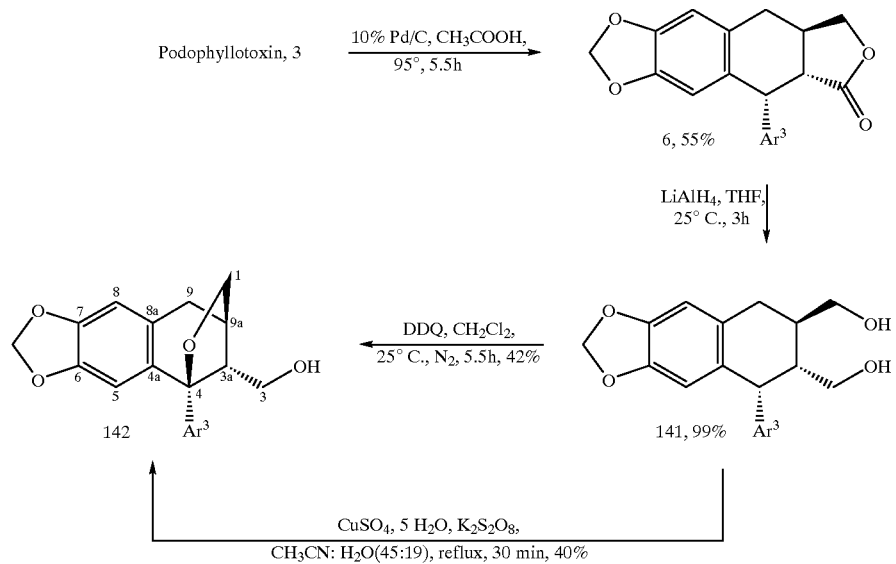

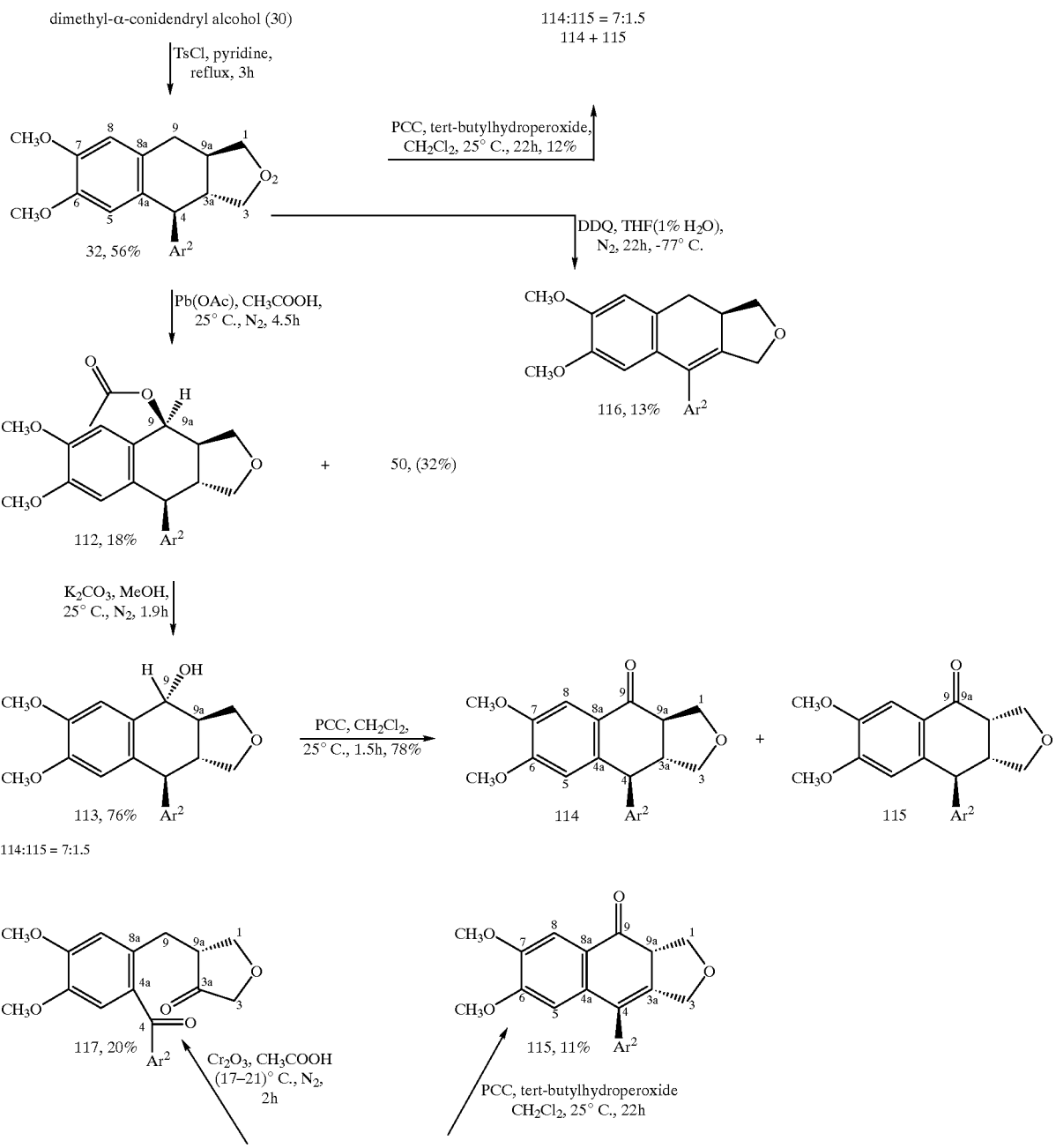

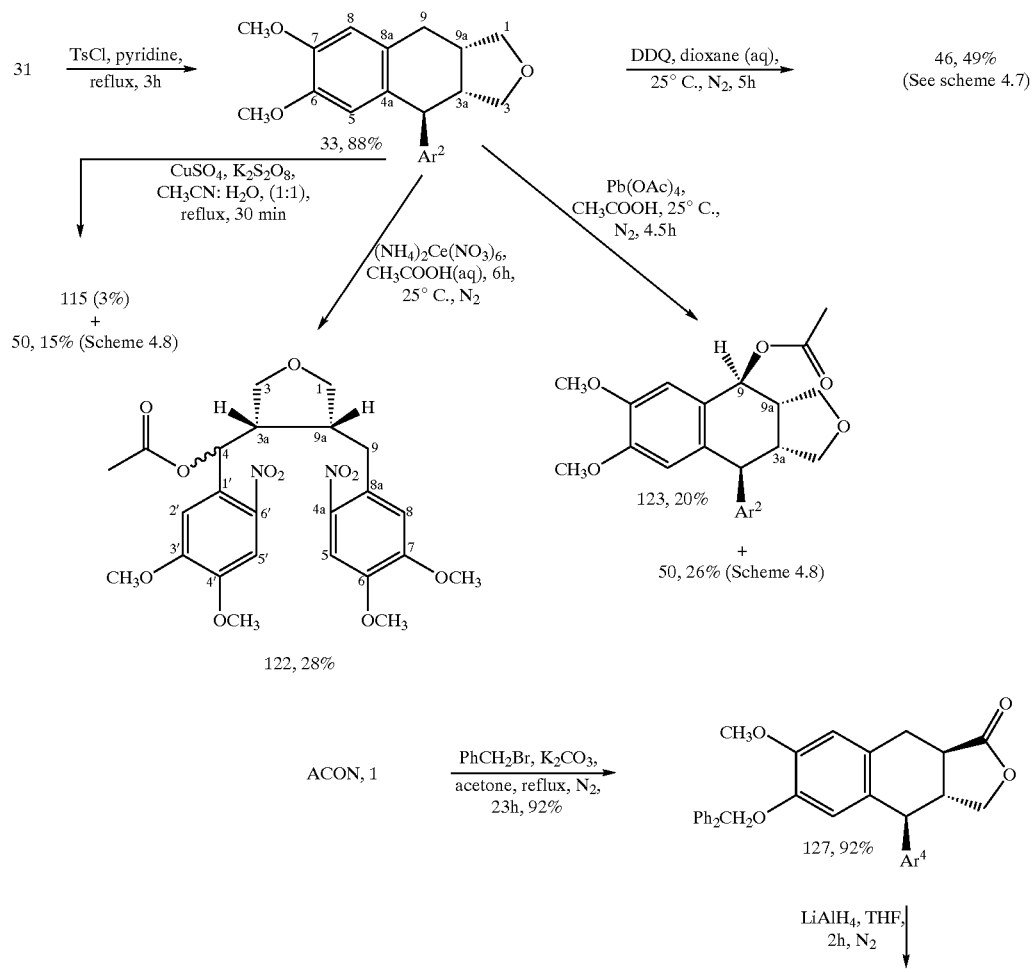

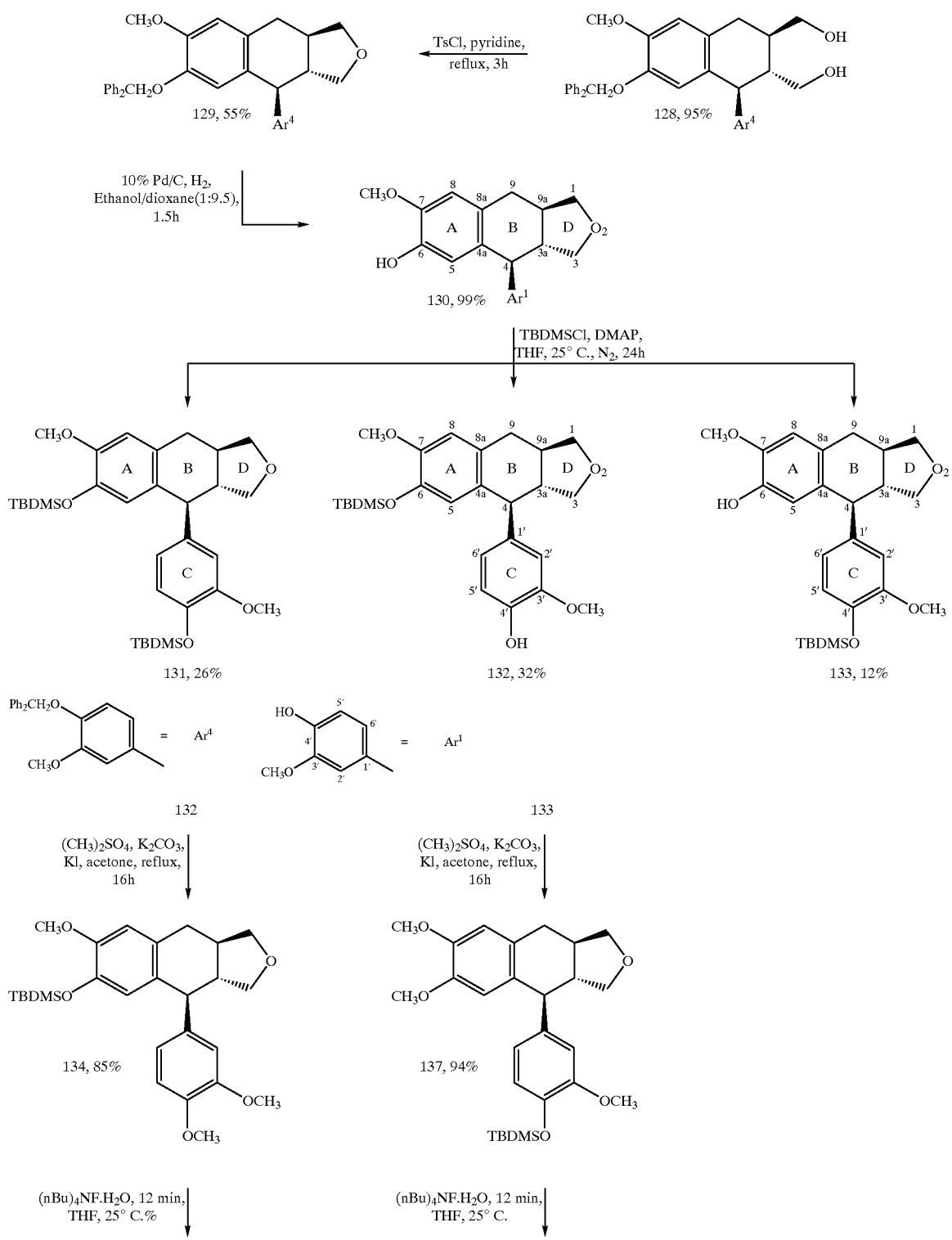

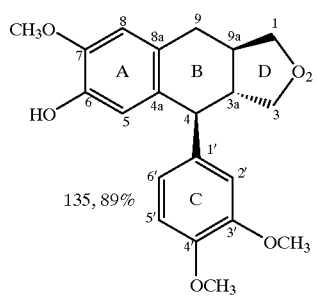
135, 89%
DDQ, dioxane (aq),
25° C., N₂, 6h
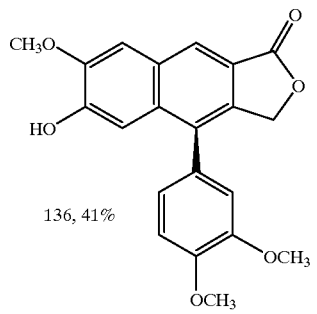
136, 41%
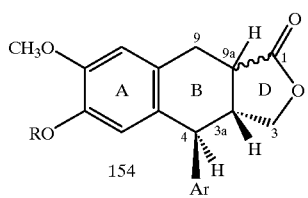
154
DDQ
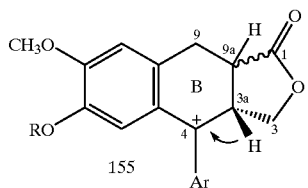
155
-continued
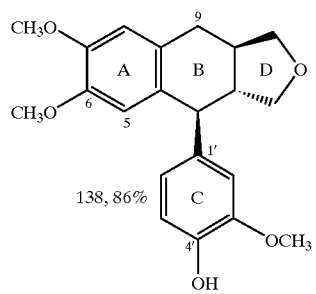
138, 86%
acetic anhydride, DMAP,
THF, 25°, 2h
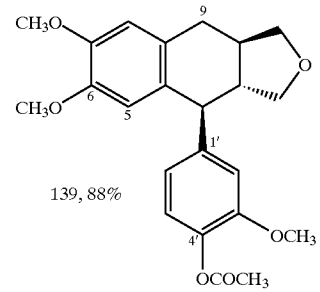
139, 88%
NBS, CH₂Cl₂,
UV light, 10 min
Complex reaction product
No pure products isolated
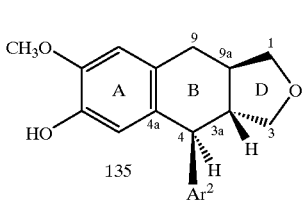
135
DDQ
Several steps
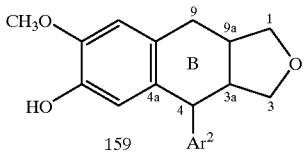
159
DDQ

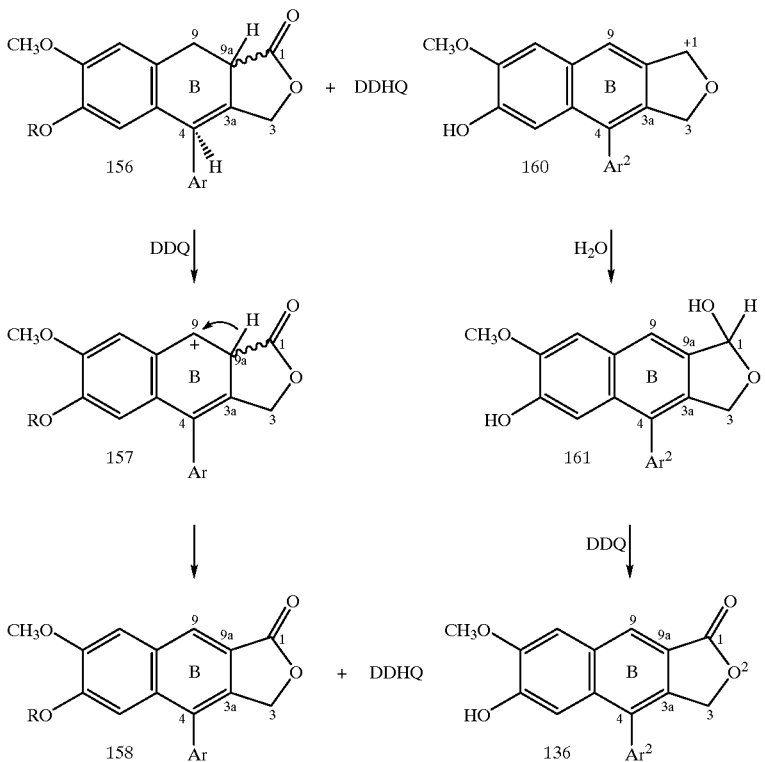

Example 1

Benzylic oxidation of 6-hydroxy-7 methoxytetralin (84) with DDQ to form 6-hydroxy-7-methoxytetralin-1-one A 89 mg (0.5 mmol) quantity of 84 was dissolved in 0.5 mL of dioxane containing 5% water. DDQ (231 mg, 1.02 mmol) was dissolved in 2 mL of dioxane containing less than 0.01% water. The solution of DDQ was added dropwise over a period of 3 minutes to the stirred solution of 6-hydroxy-7 methoxytetralin, under nitrogen. The reaction solution was stirred at 25° C. under nitrogen for 3 hours, after which time the reaction mixture was then filtered through a sintered glass funnel and the residue (DDHQ) washed with 2 mL of dioxane. The filtrate was evaporated to dryness and the residue purified by flash chromatography (EtOAc: hexane, 1:1) to give 68 mg (71% yield) of 6-hydroxy-7-methoxytetralin-1-one. mp 117–119° C., (lit. 117–119° C.); IR 3338 (O—H str.), 3013, 2945, 2871, 2841, 1664 (C=O str.), 1612, 1578, 1509, 1335, 1282, 1223, 1182, 1131, 1032, 800 cm$^{-1}$; $^1$H NMR (CDCl$_3$) δ7.51 (1H, s, H-8), 6.73 (1H, s, H-5), 6.44 (1H, s, —OH), 3.88 (3H, s, —OCH$_3$), 2.83 (2H, t, J=6.11 Hz), 2.57 (2H, t, J=6.53 Hz), 2.07 (2H, qn, J=6.34 Hz, H-3); $^{13}$C NMR (CDCl$_3$) 197.3 (C-1), 150.8, 145.7, 140.1, 125.6, 113.8, 108.5, 56.1, 38.5, 29.2, 23.7, 23.5; LRMS EI m/z 192[M$^+$, base peak], 177 [M$^+$—CH$_3$], 164 [M$^+$—CO].

Example 2

Conversion of 6-hydroxy-7-methoxytetralin (84) to 6-acetoxy-7-methoxytetralin (86)

A 250 mg (1.4 mmol) quantity of 6-hydroxy-7-methoxytetralin was dissolved in 1 mL of dry THF. To the solution of 6-hydroxy-7-methoxytetralin was added 4-dimethylaminopyridine (DMAP, 476 mg, 4.2 mmol) in 6 ml of dry THF and acetic anhydride 446 mg (4.37 mmol) in 1.5 mL, of dry THF. The reaction solution was stirred under a dry atmosphere at 25° C. for 18 hours, after which time the solvent was evaporated to dryness. The resulting residue was dissolved in EtOAc (40 mL) and the EtOAc layer washed with water (2×5 mL), 5% NaHCO$_3$ (aq) (2×5 mL), 1 M HCl (5×5 mL), water (5 mL), and brine (2×5 mL). The organic layer was dried over MgSO$_4$ and evaporated to dryness. The residue was purified by flash chromotography (hexane : EtOAc, 4:1) to give 290 mg (94% yield) of 6-acetoxy-7-methoxytetralin. IR 3003, 2930, 2860, 2840, 1767 (C=O str.), 1619, 1512, 1266, 1219, 1195, 1104, 1026; $^1$H NMR (CDCl$_{13}$) δ6.73 (1H, s), 6.66 (1H, s), 3.79 (3H, s, —OCH$_3$), 2.68–2.74 (4H, m), 2.30 (3H, s, —OCOCH$_3$), 1.78 (4H, qn, J=3.25 Hz); $^{13}$C NMR (CDCl$_3$) δ6.73 169.3, 148.6, 137.5, 135.3, 129.3, 122.8, 112.8, 55.8, 29.3, 28.4, 23.0, 20.5; LRMS EI m/z 220[M$^+$], 178 [M$^+$, base peak].

Example 3

Benzylic oxidation of 6-acetoxy-7-methoxytetralin (86) with DDQ in aqueous dioxane A 220 mg (1 mmol) quantity of 6-acetoxy-7-methoxytetralin was dissolved in 1 mL, of dioxane containing 5% water. DDQ (454 mg, 2 mmol) was dissolved in 4 mL of dioxane containing less than 0.01% water. The solution of DDQ was added dropwise over a period of 5 minutes to the stirred solution of 6-acetoxy-7-methoxytetralin at 25° C., under nitrogen. The reaction solution was stirred at 25° C. under nitrogen for 20 hours, after which time the reaction mixture was filtered through a sintered glass funnel and the precipitate (DDHQ) washed with 2 mL dioxane. The residue on evaporation of the filtrate was portioned between 10 mL 5% NaHCO$_3$ (aq) and 80 mL of EtOAc. The EtOAc layer was separated and washed with 5% NaHCO$_3$ (aq)(1×5 mL), water (1×5 mL), and brine (2×5 ml). The organic layer was dried over MgSO$_4$ and evaporated to dryness. The residue was purified by flash chromatography (hexane: EtOAc, 2.5:1.5) to give two products, 146 mg (62% yield) of 7-acetoxy-6-methoxytetralin-1-one (87) and 50 mg (23% yield) of 2-acetoxy-3-methoxy naphthalene (88). 7-acetoxy-6-methoxytetralin-1-one: mp 118.5–119.5° C.; IR 1769 (C=O str.), 1674, 1613, 1506, 1272, 1210, 1186, 1031 cm$^{-1}$; $^1$H NMR (CDCl$_3$) δ7.69 (1H, s, H-8), 6.74 (1H, s, H-5), 3.86 (3H, s, —OCH$_3$), 2.91 (2H, t, J=6.08 Hz, H-2), 2.57 (2H, t, J=6.53 Hz, H-4), 2.28 (3H, s, OCOCH$_3$), 2.11 (2H, qn, J=6.35 Hz, H-3); $^{13}$C NMR (CDCl$_3$) δ196.2 (C-1), 168.8, 155.2, 144.5, 138.7, 126.1, 121.5, 111.3, 56.0, 38.4, 29.7, 23.2, 20.4; LRMS EI m/z 234 [M$^+$], 164 [base peak]. 2-acetoxy-3-methoxy naphthalene: mp 114–116° C.; IR 1764 (C=O str.), 1633, 1508, 1483, 1371, 1261, 1201, 1108, 1015 cm$^{-1}$; $^1$H NMR (CDCl$_3$) δ7.75 (1H, dd, J=8.13, 1 Hz, H-5 or H-8), 7.73 (1H, dd, J=7.43, 1.1 Hz, H-5 or H-8), 7.50 (1H, s, H-1), 7.44 1H, ddd, J=8.23, 7.55, 1.34 Hz, H-6 or H-7), 7.36 1H, ddd, J=8.14, 7.51, 1.24 Hz, H-6 or H.7), 7.22 (1H, s, H-4), 3.95 (3H, s, —OCH$_3$), 2.38 (3H, s, —OCOCH$_3$); $^{13}$C NMR(CDCl$_3$)d 169.2, 150.2, 140.3, 132.5, 128.3, 127.2, 126.5. 124.2, 120.3, 107.3, 55.8, 20.6; LRMS EI m/z 216 [M$^+$], 174 [base peak].

Example 4

Oxidation of the C-9 position of β-conidendryl alcohol (95) with DDQ to the single bridged compound (96)

A solution of DDQ (150 mg, 0.66 mmol) in 8.5 mL of dioxane seas added to a solution of β-conidendryl alcohol (200 mg, 0.56 mmol) in 45.5 mL of dioxane. The dioxane used contained less than 0.01% water. The reaction solution Ad as stilTed under nitrogen at 25° C. for 5 hours, after which time it was evaporated to dryness. To the residue was added 50 mL of EtOAc and 25 mL of 5% NaHCO$_3$ (aq). The suspension was shaken until all the residue had dissolved. The aqueous layer was further extracted with EtOAc (3×30 mL). The combined EtOAc extracts were washed with water (1×30 mL) and brine (1×30 mL). The organic layer was dried over Na$_2$SO$_4$ and evaporated to dryness. The resulting residue was purified by preparative thin layer chromatography (EtOAc) to give 117 mg (59% yield) of the C-9 oxygenated, single-bridged compound 96. mp 167–169° C.; $[α]^{25}_D$-30.95 (c 1.58, acetone); IR 3371 (O—H str.). 3050, 2937, 2880, 2841, 1510, 1462, 1449, 1427, 1272, 1211, 1147, 1119, 1045, 877, 771 cm$^{-1}$; $^1$H NMR (methanol-d$_4$) δ6.88 (1H, s, H-5 or H-8), 6.78 (1H, d, J=8.12 Hz, H-5'), 6.72 (1H, d, J=1.87 Hz, H-2'), 6.54 (1H, s, H-5 or H-8), 6.5 (1H, dd, J=8.14, 1.88 Hz, H-6'), 4.84 (4H, s,3-OH, s and H-9), 4.18 (1H, d, J=1.65 Hz, H-4), 4.09 (1H, dd, J=8.58, 5.94 Hz, H-2), 3.94 (3H, s, —OCH$_3$), 3.83 (3H, s, —OCH$_3$), 3.75 (1H, d, J=8.57 Hz, H-2), 3.59 (1H, dd, J=10.73, 9.17 Hz., H-1), 3.38 (1H, dd, J=10.92, 6.20 Hz, H-1), 2.51–2.56 (2H, m. H-3a, H-9a); $^{13}$C NMR (pyridine-d$_5$) δ46.2 (C-3a or C-9a), 46.5 (C-3a or C-9a) 53.7 (C-4), 56.4 (—OCH$_3$), 56.5 (—OCH$_3$), 62.7 (C-1), 71,8 (C-2), 79.1 (C-9), 112.2 (C-5 or C-8), 114.1 (C-2'), 116.8 (C-5'), 119.6 (C-5 or C-8), 122.8 (C-6'), 130.6, 133.5, 138.0, 147.2, 147,8, 148.5, 149.0; HRMS EI m/z [M$^+$] Calcd. For C$_{20}$H$_{22}$O$_6$: 358.1416, found 358.1417 (0.3 ppm deviation, base peak), 326.1, 297.1, 265.1, 237.1, 203.1, 175.1, 137.1, 175.1, 137.1, 115.1, 89.0, 77.0.

Example 5

Conversion of Dimethyl-α-Coindendryl Alcohol to 6-Oxabicyclo[3.2.1]octane Incorporating a Single Methylenieoxy Bridge Wherein the Oxygen Atom Extends to the Benzhydrylic Carbon Atom 360 mg of dimethyl-α-conidendryl alcohol was dissolved in 54 mL of a mixture of dry methylene chloride and dry tetrahydrofuran in a ratio of 39 to 15, and a solution of 246 mg of 2,3-dichloro-5,6-dicyanoquinone in 8.1 mL of dry methylene chloride was added. The solution was stirred at 25° C. in an atmosphere of dry nitrogen for 3 hours. Thereafter, the reaction mixture was evaporated to dryness at reduced atmospheric pressure, and the residue as treated with a mixture of 33 mL of 5% aqueous sodium bicarbonate and 30 mL of ethyl acetate. The aqueous and organic phases were separated, and the aqueous phase was extracted several times with 4 mL volumes of ethyl acetate. The combined ethyl acetate extracts were washed twice with 15 mL of water and thereafter twice with 15 mL portions of water, and then brine. The organic phase was dried over anhydrous sodium sulfate, and thereafter, the solvent was removed at reduced atmospheric pressure. The resulting residue was subsequently chromatographed on a column of silica gel at medium pressure. whereby a mixture of methylene chloride and ethyl acetate in a ratio of 1 to 1 was continuously used as an eluant. First eluted from the column was the minor product, the dioxatricyclodecane derivative. Thereafter, eluted the pure major product, the oxabicyclooctane derivative having a melting point of 165–172° C. and an optical rotation of $[α]^{25}_D$+72.5 (acetone, c 1.71). HRMS [M$^+$] Calcd. For C$_{22}$H$_{26}$O$_6$: 386.1729, Found: 386.1738.

Example 6

Conversion of 9-deoxypodophyllol to 6-Oxabicyclo [3.2.1]octane incorporating a Single Methyleneoxy Bridge wherein the Oxygen Atom Extends to the Benzhydrylic Carbon Atom 123 mg of 9-deoxypodophyllol was dissolved in 18 mL of dry methylene chloride, and a solution of 82 mg of 2,3-dichloro-5,6-dicyanobenzoquinone in 2.7 mL of dry methylene chloride was added. The mixture was stirred at 22° C. in an atmosphere of dry nitrogen for 20 hours. Thereafter, the reaction mixture was processed in the manner described in Example 5 using volumes of extraction solvents, reagents, water, and brine in proportion to the amounts of starting diol and oxidizing agent used in this example. The resulting residue after processing was chromatographed on a silica gel plate (GF, 20×20 cm, 500μ), whereby distilled acetone was used as the developing solvent. Removal of the major band from the plate followed by separation of the major product from the silica gel by extraction of the latter with distilled acetone gave the pure oxabicylooctane derivative having a melting point of 148–149° C. and an optical rotation of $[α]^{25}_D$=+44.2 (acetone, c 1.19). HRMS Calcd. For C$_{22}$H$_{24}$O$_7$: 400.1522, Found: 400.1526.

Example 7

Conversion of Dimethyl-α-conidendryl Alcohol to its 3.8-Dioaxatricyclo[5.3.0.0$^{4,10}$]-decane Derivative Incorporating Two Methyleneoxy Bridges 116 mg of dimethyl-α-conidendryl alcohol was dissolved in 45 mL of acetonitrile, and a solution of 75 mg of copper sulfate pentahydrate in 5 mL of water and 161 mg of potassium peroxydisulfate in 14 ml of water were added in succession with stirring. The stirred solution was heated to reflux for 30 minutes. Thereafter, the solution was cooled to 25° C., and 20 mL of water was added. The resulting mixture was extracted four times with 15 mL portions of etyl acetate, and the combined ethyl acetate extracts were washed successively with 10 mL of water and 10 mL of brine. The organic phase layer was dried over anhydrous magnesium sulfate, and thereafter, evaporated to dryness at reduced atmospheric pressure. The resulting residue was subsequently chromatographed on a column of silica gel at medium pressure, whereby a mixture of methylene chloride and ethyl acetate in a ration of 3 to 1 was continuously used as an eluant to give 44 mg of dioxatricyclodecane derivative having a melting point of 165 –166° C. and an optical rotation of $[\alpha]^{25}_D$ –6.07 (acetone, c 2.5). HRMS Calcd. For $C_{22}H_{24}O_6$: 384.1573, Found: 384.1572.

Example 8

Conversion of 9-Deoxypodophyllol to 3,8-Dioxatricyclo[5.3.0.0$^{4,10}$]decane Derivative Incorporating Two Methyleneoxy Bridges 2.67 g of 9-deoxypodophyllol was dissolved in 300 mL of acetonitrile, and a solution of 1.66 g of copper sulfate pentahydrate and 3.58 g of potassium peroxydisulfate in 200 mL of water was added. The stirred solution was heated at reflux for 45 minutes. Thereafter, the solution was cooled to 25° C., and concentrated at reduced atmospheric pressure. The resulting mixture was extracted with ethyl acetate. The organic phase was washed successively with water and brine. The organic phase layer was separated, and was dried over anhydrous sodium sulfate. Thereafter, the solvent was evaporated at reduced atmospheric pressure. The resulting residue was chromatographed on a column of silica gel at medium pressure, using a solvent consisting of hexane and ethyl acetate in a ration of 1 to 1 giving 20 mg of the dioxatricyclodecane derivative having a melting point of 165–166° C. and an optical rotation of $[\alpha]^{25}_D$ –5.2 (acetone, c 0.59). HRMS Calcd. For $C_{22}H_{24}O_7$: 398.1365, Found: 398.1365.

Example 9

Conversion of 9-Deoxysikkimol to Two Different 6-Oxabicyclo[3.2.1]octane Derivatives 164 mg of 9-deoxysikkimol was dissolved in 60 mL of the solvent methylene chloride, and a solution of 98 mg of 2,3-dichloro-5.6-dicyanobenzoquinone in 20 mL of methylene chloride was added. The mixture was stirred at 25° C. in an atmosphere of dry nitrogen for 3 hours. Thin layer chromatography indicated no unconverted 9-deoxysikkimol remained. Thereafter, the reaction mixture was processed in the manner described in Example 5 using volumes of extraction solvents, reagents, water, and brine in proportion to the amounts of reactants used in Example 5. The residue resulting from processing was chromatographed on a silica gel plate (GF, 20×20 cm, 500μ), whereby a mixture of methylene chloride and ethyl acetate in the ratio of 1 to 1 was used as the developing solvent. Two separate bands each consisting of a product absorbed on the silica gel were removed from the plate. Each product was separated by extraction of the removed silica gel with methylene chloride. Thereafter, evaporation of methylene chloride from each extract at reduced atmospheric pressure gave two different and pure oxabicyclooctanes. Obtained was 53 mg of oxabicyclooctane wherein the oxygen atom of the methyleneoxy-bridge was bonded to the benzhydrylic carbon atom, a glass-like residue having $[\alpha_D]$=+66.5° C. (CHCl3, c 3.4). HRMS [MNa$^+$] Calcd for $C_{23}H_{28}O_7Na$: 439.1733. Found: 439.1737. Also obtained was 72 mg of the oxabicyclooctane wherein the oxygen atom of the methyleneoxy bridge was bonded to the benzylic carbon atom, a glass-like residue having $[\alpha_D]$=8.6°(CHCl3, c 1.8)]. HRMS (MNa$^+$] Calcd. for $C_{23}H_{28}O_7Na$: 439.1733. Found: 439.1731.

Example 10

Conversion of 9-Deoxypicropodophyllol to Two Different 6-Oxabicyclo[3.2.1]octane Derivatives 380 mg of 9-deoxypicropodophyllol was added to 50 mL of acetonitrile, and the resulting mixture was heated to reflux until all the solid dissolved. The stirred solution was cooled to about 45° C., and a solution of 240 mg copper sulfate pentahydrate in 10 mL of water was added followed immediately by a solution of 510 mg of potassium peroxydisulfate in 10 mL of water. The stirred mixture was heated to reflux tinder an atmosphere of nitrogen for 0.5 hour, and thereafter, was cooled to 25° C. and extracted four times with 10 mL portions of ethyl acetate. The combined extracts were processed in the manner indicated in previous Examples and the residue was chromatographed on a column of silica gel eluted with a mixture of ethyl acetate and methylene chloride in ratio of 1:1. The fraction consisting of a mixture of the two, isomeric 6-oxabicyclo [3.2.1 ]octane derivatives was separated into the pure derivatives by preparative thin layer chromatography using a mixture of ethyl acetate and methylene chloride in a ratio of 1 to 1. Eluting first on the plate with an $R_f$=0.5 was the derivative (11 mg) wherein methyleneoxy bridging extended to the benzhydrilic carbon atom, and having a melting point of 84–86° C. and a rotation of $[\alpha_D]$=–23.7° (CHCl3, c 0.9). HRMS [M$^+$] Calcd. for $C_{22}H_{24}O_7$: 400.1522. Found: 400.1534. Elutin second with an $R_f$=0.3 was the derivative (45 mg) wherein methyleneoxy brideging, extended to the benzylic carbon atom, and having a melting point of 71–72° C. and a rotation of $[\alpha]_D$=+88.5 (CHCl3, c 1.1). HRMS [M$^+$] Calcd. for $C_{22}H_{24}O_7$: 400.1522. Found: 400.1521.

Example 11

Conversion of Two Different 6-Oxabicyclo[3.2.1] octane Derivatives from 9-Deoxysikkimol to the same 3.8-Dioxatricyclo[5.3.0.0$^{4,10}$]decane Derivative:

a. From the 6-Oxabicyclooctane Derivative wherein Methyleneoxy Bridging Extends to the Benzhydrylic Carbon Atom A mixture of 34 mg of copper sulfate pentahydrate and 73 mg of potassium peroxydisulfate in 8 mL of water was added to a solution of 53 mg of the 6-oxabicyclooctane dissolved in 20 mL of acetonitrile. The resulting mixture was heated to reflux and stirred under an atmosphere of nitrogen for 0.5 hour. Thereafter, the mixture was cooled to 24° C. 10 mL of water was added and the resulting mixture was extracted three times with 15 mL portions of ethyl acetate. The combined organic phase was washed with 10 mL of 5% aqueous sodium bicarbonate, twice with water, and once with 5 mL of brine. The processed organic solution was dried over anhydrous sodium sulfate. Thereafter, the solvent was evaporated at reduced atmospheric pressure. The residue was purified on a silica gel preparative TLC plate using a mixture of ethyl acetate and methylene chloride in a ratio of 1 to 5 as the developing solvent. Thereby 28 mg of the 3,8-dioxatricyclodecane was obtained as a glass-like residue having an optical rotation $[\alpha_D]$=+21.6° (CHCl3, c 0.5). HRMS [MNa$^{30}$] Calcd. for $C_{23}H_{26}O_7Na$: 437.1576. Found: 437.1583.

b. From the 6-Oxabicyclooctanie Derivatlie wherein Methyleneoxy Bridging Extends to the Benzylic Carbon Atom A mixture of 48 mg of copper sulfate pentahydrate and 106 mg of potassium peroxydisulfate in 12 mL of water was added to a solution of 70 mg of the 6-oxabicyclooctane dissolved in 28 mL of acetonitrile. Reaction conditions and the processing procedure were the same as those given in Part a, except volumes of solvents were adjusted for the larger amount of starting amounts 6-oxabicyclooctane and oxidant. Thereby, 42 mg of the 3,8-dioxatricyclooctane was obtained as a glass-like residue having an optical rotation $[\alpha_D]$=+19.60° (CHCl3, c 3.4).

Example 12

Conversion of the 6-Oxabicyclo[3.2.1]octane Derivative of Dimethyl-α-conidendryl Alcohol to an Ester 100 mg of the 6-oxabicyclooctane derivative of dimethyl-α-conidendryl alcohol was dissolved in 100 mL of dry tetrahydrofuran, and the resulting solution was added to a mixture of 65 mg of dimethylaminopyridine and 56 mg of acetic anhydride in 0.5 mL of dry tetrahydrofuran. The resulting solution was stirred at 25° C. under an atmosphere of dry nitrogen for 2 hours. Thereafter, the tetrahydrofuran was evaporated at reduced atmospheric pressure, and the resulting residue was dissolved in diethyl ether. The ether solution was washed successively with two 6 mL amounts of 5% aqueous sodium bicarbonate, five 6 mL amounts of 1 M, aqueous hydrochloric acid, water, and brine. The organic phase was separated, and then it was dried over anhydrous sodium sulfate. The solvent was evaporated at reduced atmospheric pressure to obtain 95 mg of pure acetate ester having a melting point of 143.5–144.5° C., and having an optical rotation of $[\alpha]^{25}_D$+101.5° (acetone, c 2.05). HRMS [M$^+$] Calcd for $C_{24}H_{28}O_7$: 428.1835. Found: 428.1860.

Example 13

Conversion of the 6-Oxabicyclo[3.2.1]octane Derivative of Dimethyl-α-conidendryl Alcohol to a Silyl Ether 413 mg of t-butyldimethylsilyl chloride dissolved in 3.6 mL of dry tetrahydrofuran was added to a solution of 288 mg of the oxabicyclooctane derivative of dimethyl-α-conidendryl alcohol in a mixture of 378 mg of dimethylaminopyridine and 6 mL of dry tetrahydroftiran under an atmosphere of dry nitrogen. The resulting mixture was stirred at 25° C. under an atmosphere of dry nitrogen for 24 hours. Thereafter, 40 mL of 5% aqueous sodium bicarbonate was added, the aqueous layer was separated and then extracted five times with 20 mL portions of ethyl acetate. The combined ethyl acetate extracts were washed twice with 70 mL portions of water and subsequently washed twice with 20 mL portions of brine. The organic phase was dried over anhydrous sodium sulfate, and thereafter, the solvent was evaporated at reduced atmospheric pressure. The resulting residue was chromatographed on a column of silica gel at a moderate positive pressure. whereby a mixture of hexane and ethyl acetate in a ratio of 1 to 1 was continuously used as an eluant to give 349 mg of the pure t-butyldimethylsilyl ether, a viscous oil, having $[\alpha]^{25}_D$ +31.2° (CHCl$_3$, c 1.25). HRMS [M$^+$] Calcd for $C_{28}H_{40}O_6$ Si: 500.2594. Found: 500.2587.

Example 14

Conversion of Podophyllol through Dehydration followed by Oxygenation to the 3,8-Dioxatricyclo [5.3.0.0$^{4,10}$]decane Derivative 187 mg of podophyllol ($[\alpha]_D^{25}$=−180° (CHCl$_3$, c 0.7)) incorporating two methyleneoxy bridges was prepared by the lithium aluminum hydride reduction of 205 mg of podophyllotoxin in dry tetrahydrofuran. Five drops of 1N aqueous hydrogen chloride was added to a solution of 185 mg of the podophyllol. The resulting mixture was stirred and heated to reflux under an atmosphere of nitrogen for 1 h. Thin layer chromatography on silica gel eluted with ethyl acetate indicated no podophyllol (R$_f$ 0.35) remained. After cooling the mixture, it was washed three times with 15 mL portions of water. The combined aqueous wash was extracted three times with 10 mL portions of ethyl acetate. The combined ethyl acetate extract was added to the chloroform solution and the resulting mixture was washed once with 10 mL of water and then 10 mL of brine, and thereafter dried over anhydrous magnesium sulfate. Removal of the magnesium sulfate by filtration and evaporation of the solvent from the filtrate at reduced atmospheric pressure gave 153 mg of the 6-oxabicyclo[3.2.1]octane ($[\alpha]_D$=+183° (CHCl$_3$, c 2.9); R$^f$ 0.60, ethyl acetate) wherein the oxygen of the methyleneoxy bridge had bonded to the benzylic carbon. This intermediate was used in the next step without further purification.

A suspension of 150 mg of the oxabicyclooctane in 55 mL of acetonitrile was stirred and warmed until solution resulted. Thereafter, the solution was cooled to 45° C. and then a solution containing 94 mg of copper sulfate perhydrate and 203 mg of potassium peroxydisulfate in 24 mL of water was added. Thereafter, the stirred mixture was heated to reflux under an atmosphere of nitrogen for 0.5 hour and then cooled to 25° C. and 24 mL of water was added. The resulting mixture was extracted four times with 25 mL of ethyl acetate. The combined extracts were washed successively with 20 mL of 5% aqueous sodium bicarbonate, twice with 20 mL volumes of water, once with 10 mL of brine, and dried over anhydrous magnesium sulfate. The magnesium sulfate was removed by filtration and the solvent was evaporated from the filtrate at reduced atmospheric pressure. The residue was chromatograplhed on a column of silica gel under moderate positive pressure using an eluting solvent of ethyl acetate and methylene chloride in a ratio of 1 to 10. A 50 mg amount of the dioxatricyclodecane $[\alpha]_D^{25}$=−28.90° (CHCl$_3$, c 3.4) of the dioxatrlcyclodecane was obtained.

Example 15

Directed Benzylic Oxytzeenations of Tetrahydroniaphthalenes: Control by Aromatic Ring Substitutions a. Formation of 6-Hydroxy-7-methoxytetralin-1-one from 6-Hydroxy-7-methoxy-1, 2, 3, 4-tetrahydronaphthalene.

A solution of 231 mg of 2,3-dichloro-5,6-dicyanobenzoquinone in 2 mL of dioxane was added dropwise over a period of 3 minutes to a stirred solution of 89 mg of 6-hydroxy-7-methoxytetralin dissolved in 5% aqueous dioxane under an atmosphere of nitrogen. The resulting solution was stirred at 25° C. under nitrogen for 3 hours. Thereafter the reaction mixture was filtered through a sintered glass funnel and the solid residue of 2,3-dichloro-5,6-dicyanodihydrobenzoquinone was washed with 2 mL of dioxane. The residue wash solution was combined with the filtrate. Thereafter the dioxane was evaporated from the combined filtrate at reduced atmospheric pressure. The resulting residue was chromatographed on a column of silica gel eluted with a solution of ethyl acetate and hexane in ratio of 1 to 1 to obtain 68 mg of known 6-hydroxy-7-methoxytetralin-1-one having m.p. 117–119° C. (lit. 117–119° C. Grethe, G. et al *J Org. Chem*, 1968, 33 504–508.)

b. The Two Step Formation of 6-Methoxy-7-hydroxytetralin-1-one from 6-Acetoxy-7-Methoxy-1, 2, 3, 4-tetrahydronaphthalene A solution of 454 mg of 2,3-dichloro-5,6-dicyanobenzoquinone in 4 mL of dioxane was added dropwise over a period of 5 minutes to a stirred solution of 6-acetoxy -7-methoxytetralin in 1 mL of 5% aqueous dioxane at 25° C. under an atmosphere of nitrogen. The resulting solution was stirred at 25° C. for 20 hours. Thereafter the reaction mixture was filtered through a sintered glass funnel and the solid residue of 2,3-dichloro-5,6-dicyaniodihydroquinione was washed with 2 mL of dioxane. The residue wash solution was combined with the filtrate. Thereafter the dioxanie was evaporated from the combined filtrate at reduced atmospheric pressure. The resulting residue was stirred with a mixture of 10 mL of 5% aqueous sodium bicarbonate and 80 mL of ethyl acetate. The ethyl acetate layer was separated and washed successively once with 5 mL of 5% aqueous sodium bicarbonate, once with 5 mL of water, and twice with 5 mL of brine. The ethyl acetate extract was dried over anhydrous magnesium sulfate. The magnesium sulfate was removed by filtration and the ethyl acetate was evaporated from the filtrate at reduced atmospheric pressure. The resulting residue was chromatographed on a column of silica gel eluted by a solution of ethyl acetate and hexane in a ratio of 3 to 5 under a moderate positive pressure to obtain 146 mg of 7-acetoxy-6-methoxytetralin-1-one having m.p. 118.5–119.5° C. MS [M+]234.

3.5 mL of water and then 3.5 mL of saturated aqueous sodium bicarbonate was added to 117 mg of 7-acetoxy-6-methoxytetralin- 1-one dissolved in 7 mL of methanol. The resulting solution was stirred under nitrogen at 25° C. for 17 hours. Thereafter the solution was acidified with aqueous hydrogen chloride and extracted five times with 6 mL portions of methylene chloride. The combined methylene chloride extracts were washed once with brine and dried over anhydrous magnesium sulfate. The dried extract was separated by filtration and the methylene chloride was removed from the filtrate by evaporation at reduced atmospheric pressure and gave 94 mg of 6-methoxy-7-hydroxytetralin-1-one having m.p. 151–152° C.

Example 16

In Vitro and In Vivo Testing

Derivatives of tetrahydronaphthalene lignans were tested in the National Cancer Institute (NCI) screen program to demonstrate antiproliferative activity in vitro through its 60 human tumor cell line screen and in vivo using hollow fiber assays. A $GI_{50}$ ranging from less than $10^{-8}$ to $10^{-5}$ molar was observed for 26% of cell lines for the podophyllotoxin derived oxabicyclooctane wherein the methylene oxybridge was directed to the benzhydrylic carbon.

The NCI In Vivo Screening Procedure is described in Monks et al., *J. Natl. Cancer Inst.*, 83: 488–601 (1988), as are the origins and processing of the cell lines. In summary, cell suspensions that are diluted according to the particular cell type and the expected target cell density (5000–40,000 cells per well based on cell growth characteristics) are added by pipet (100 μL) into 96-well microtiter plates. Inoculates are allowed a preincubation period of 24 hours at 37° C. for stabilization. Dilutions at twice the intended test concentration were added at time zero in 100 μL aliquots to the microtiter plate wells. Usually, test compounds are evaluated at five 10-fold dilutions. In routine testing, the highest well concentration is $10^{-4}$ M, but for the standard agents the highest well concentration used depends on the agent. Incubations last for 48 hours in 5% $CO_2$ atmosphere and 100% relative humidity. The cells are assayed by using the sulforhodamine B assay. A plate reader is used to read the optical densities, and a microcomputer processes the optical densities into the special concentration parameters. Results of such in vitro screening with compounds of the present invention are summarized in Table 3.

TABLE 3

$GI_{50}{}^a$ Values in Molarity$^b$ of Tetrahydronaphthalene (THN) Lignan-Derived Oxabicyclooctane (OBO) and Dioxatricyclodecanes (DTD).

| | | Derivative Type | | Bridge$^c$ Extends to: | | | |
|---|---|---|---|---|---|---|---|
| No. | THN Class | OBO | DTD | Benzylic | Benzhydrylic | $GI_{50}$ | %$^d$ |
| 1 | podophyllotoxin | | Y | Y | Y | <$10^{-8}$ | 69 |
| | | | | | | <$10-8$ | 83 |
| 2 | podophyllotoxin | Y | | | Y | $10^{-5}$–$10^{-8}$ | 12 |
| | | | | | | $10^{-5}$–$10^{-8}$ | 26 |
| 3 | picropodophyllin | Y | | Y | | $10^{-5}$–$10^{-6}$ | 93 |
| 4 | α-conidendrin | | Y | Y | Y | >$10^{-4}$ | 100 |
| 5 | α-conidendrin | Y | | | Y | >$10^{-4}$ | 96 |
| 6 | α-conidendrin$^e$ | Y | | | Y | $10^{-5}$–$10^{-6}$ | 10 |
| 7 | β-conidendrin | Y | | Y | | >$10^{-4}$ | 100 |
| 8 | β-conidendrin | Y | | | Y | >$10^{-4}$ | 100 |

$^a$Growth Inhibition, 50%
$^b$Given as: a concentration range; more than the given concentration value (>); or less than the given concentration value (<).
$^c$Ring carbon atom type to which the oxygen of a methyleneoxy bridge is attached.
$^d$Percentage of cell lines affected at the given concentration.
$^e$As an acetate ester of the preceding compound in the table.

Preliminary in vivo testing was conducted by the hollow fiber assay on the oxabicyclooctane and the dioxatricyclodecanes identified as sufficiently active in the large scale in vitro cell screens. Each compound is tested against a standard panel of 12 human tumor cell lines, including NCI-H23, NCI-H22, MDA-MB-231, MDA-MB-435, SW-620, COLO 205, LOX IMVI, UACC-62, OVCAR-3, OVCAR-5, U251, and SF-295. The cell lines are cultivated in RPMI-1640 containing 10% FBS and 2 mM glutamine. On the day preceding hollow fiber preparation, the cells are given a supplementation of fresh medium to maintain log phase growth. For fiber preparation, the cells are harvested by standard try psinization technique and resuspended at the desired density, which varies by cell line between 2–10×$10^6$ cells/mL. The cell suspension is flushed into 1 mm I.D. polyvinylidene hollow fibers with a molecular weight exclusion of 500,000 Da. The hollow fibers were heat-sealed at 2 cm intervals and the samples generated from these seals were placed into tissue culture medium and incubated at 37° C. in 5% $CO_2$ for 24 to 48 hours prior to implantation. A total of 3 different tumor lines are prepared for each experiment so that each mouse receives 3 intraperitoneal implants (1 of each tumor line) and 3 subcutaneous implants (1 of each tumor line). On the day of implantation, samples of each tumor cell line is quantitated for viable cell mass by a stable endpoint MTT assay so that the time 0 cell mass is known. Thus, the cytostatic and cytocidal capacities of the test compound can be assessed. Mice are treated with experimental agents starting on day 3 or 4 following fiber implantation and continuing once daily for a total of 4 doses. Each agent is assessed by intraperitoneal injection at 2 dose levels with 3 mice/dose/experiment. Vehicle controls consist of 6 mice receiving the compound diluent only. The fibers are collected from the mice on the day following the fourth compound treatment and subjected to the stable endpoint MTT assay. The optical density of each sample is determined spectropphotomnetrically at 540 nm and the mean of each treatment group is calculated. The percent net cell growth in each treatment group is calculated and compared to the percent net cell growth in the vehicle treated controls. Each compound is assessed in a total of 4 experiments (3 cell lines/experiment×4 experiments=12 cell lines). The oxabicyclooctane received an intraperitoneal score of 14 and a subcutaneous score of 2. The compound was found cyticidal.

It should be appreciated that the substituted derivatives of α-conindendrin, β-conindendrin, sikkimotoxin, and podophyllotoxin can be substituted by any of the $R^1$–$R^{18}$ substituients defined herein to produce the desired bridged compounds of the present invention. Although the invention has been described in detail for the purpose of illustration, it is understood that such detail is solely for that purpose, and variations can be made therein by those skilled in the art without departing form the spirit and scope of the invention which is defined by the following claims.

What is claimed:

1. A dioxatricyclodecane having two methyleneoxy bridges and comprising the formula:

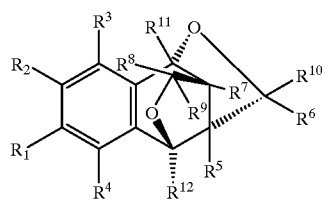

wherein $R^1$ and $R^2$ together with the atoms to which they are bonded form a substituted or unsubstituted homocyclic or heterocyclic saturated, unsaturated, or aromatic ring, or $R^1$ and $R^2$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^a$, where $R^a$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^3$, $R^4$, and $R^7$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^b$, where $R^b$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^5$ and $R^6$ together with the atoms to which they are bonded form a substituted of unsubstituted, homocyclic or heterocyclic, saturated, unsaturated, or aromatic ring, or $R^5$ and $R^6$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^c$, where $R^c$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^8$ and $R^9$ together with the atoms to which they are bonded form a substituted of unsubstituted, homocyclic or heterocyclic, saturated, unsaturated, or aromatic ring, or $R^8$ and $R^9$ are independently selected from the group consisting of hydrogen; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^d$, where $R^d$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^{10}$ and $R^{11}$ together with the atoms to which they are bonded form a substituted of unsubstituted, homocyclic or heterocyclic, saturated, unsaturated, or aromatic ring, or $R^{10}$ and $R^{11}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^e$ where $R^e$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^{12}$ is a group having the formula:

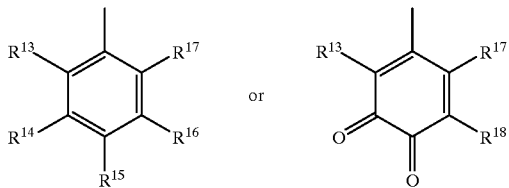

$R^{13}$, $R^{14}$, $R^{17}$, and $R^{18}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^f$, where $R^f$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^{15}$ and $R^{16}$ are independently selected from the group consisting of hydroxy; substituted or unsubstituted alkoxy; substituted or unsubstituted arylxoxy; and substituted or unsubstituted aralkoxy; or $R^{15}$ and $R^{16}$, together, have the formula —O—Z—O— where Z is a substituted or unsubstituted alkylene moiety.

2. A compound according to claim 1, wherein $R^1$ is alkoxy, aryloxy, alkenyldioxy, aralkenyldioxy, or cycloalkenyldioxy, where the aromatic ring may optionally be substituted by one or more of hydroxy, alkyl, alkoxy, nitro, amine, phenylalkyl, or halogen radicals.

3. A compound according to claim 1, wherein $R^2$ is alkoxy, aryloxy, alkenyldioxy, aralkenyldioxy, or cycloalkenyldioxy, where the aromatic ring may optionally be substituted by one or more of hydroxy, alkyl, alkoxy, nitro, amine, phenylalkyl, or halogen radicals.

4. A compound according to claim 1, wherein $R^1$ and $R^2$ are methoxy groups.

5. A compound according to claim 1, wherein $R^1$ is connected to $R^2$ as in a methylenedioxy group.

6. A compound according to claim 1, wherein $R^{14}$, $R^{15}$, and $R^{16}$ are all hydrogens, a combination of two hydrogens and one hydroxy, alkoxy, or aryloxy group, a combination of one hydrogen and two hydroxy, alkoxy, arlyoxy, alkenyldioxy, aralkenyldioxy, or cycloalkenyldioxy groups, where the aromatic ring may optionally be substituted by one or more hydroxy, alkyl, alkoxy, nitro, or halogen radicals.

7. A compound according to claim 1, wherein $R^{14}$, $R^{15}$, and $R^{16}$ are all hydroxy, alkoxy, aralkyloxy, or a combination of any one moiety with different moieties, where the aromatic ring may optionally be substituted by one or more hydroxy, alkyl, alkoxy, nitro, or halogen radicals.

8. A compound according to claim 1, wherein $R^{14}$, $R^{15}$, and $R^{16}$ are methoxy groups.

9. A method of killing cancer cells comprising:
    contacting cancer cells with a compound according to claim 1 under conditions effective to kill the cancer cells.

10. A method for making a dioxatricyclodecane having two methyleneoxy bridges according to claim 1 comprising:
    providing a tetrahydronaphthalene derivative diol wherein the diol is selected from the group consisting of α-conindendrin, sikkimotoxin, podophyllotoxin, and derivatives thereof and
    introducinig an oxidizing agent to the diol under conditions effective to form the dioxatricyclodecane having two methyleneoxy bridges.

11. A method according to claim 1, wherein the oxidizing agent is selected from the group consisting of 2,3-dichloro-5,6-dicyano-1,4-benzoquinone and copper sulfate/potassium peroxydisulfate.

12. A method according to claim 1, wherein the dioxatricyclodecane having two methyleneoxy bridges is formed at a temperature between about 22° C. and 80° C.

13. A method for making a dioxatricyclodecane having two methyleneoxy bridges according to claim 1 comprising:
    providing a compound having the formula:

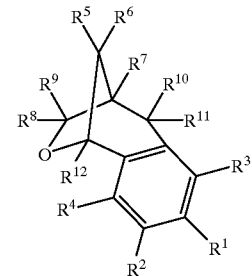

wherein
    $R^1$ and $R^2$ together with the atoms to which they are bonded form a substituted of unsubstituted homocyclic or heterocyclic saturated, unsaturated, or aromatic ring, or $R^1$ and $R^2$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^a$, where $R^a$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^3$, $R^4$, and $R^7$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^b$, where $R^b$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^5$ and $R^6$ together with the atoms to which they are bonded form a substituted of unsubstituted, homocyclic or heterocyclic, saturated, unsaturated, or aromatic ring, or $R^5$ and $R^6$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^c$, where $R^c$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^8$ and $R^9$ together with the atoms to which they are bonded form a substituted of unsubstituted, homocyclic or heterocyclic, saturated, unsaturated, or aromatic ring, or $R^8$ and $R^9$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^d$, where $R^d$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^{10}$ and $R^{11}$ together with the atoms to which they are bonded form a substituted of unsubstituted, homocyclic or heterocyclic, saturated, unsaturated, or aromatic ring, or $R^{10}$ and $R^{11}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^e$ where $R^e$ is selected from the group consisting of substituted or unsubstituted alkyl; substituted or unsubstituted aralkyl; substituted or unsubstituted aryl; a substituted or unsubstituted saturated, unsaturated, or aromatic heterocyclic group;

$R^{12}$ is a group having the formula:

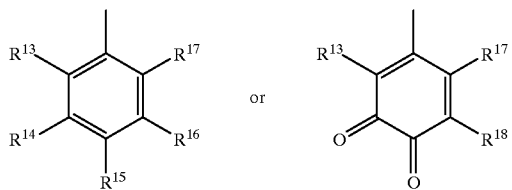

$R^{13}$, $R^{14}$, $R^{17}$, and $R^{18}$ are independently selected from the group consisting of hydrogen; hydroxy; substituted or unsubstituted alkyl; substituted or unsubstituted aralkyl; substituted or unsubstituted aryl; a substituted or unsubstituted saturated, unsaturated, or aromatic heterocyclic group; substituted or unsubstituted alkoxy; substituted or unsubstituted arylxoxy; substituted or unsubstituted aralkoxy; substituted or unsubstituted alkylthio; substituted or unsubstituted arylthio; substituted or unsubstituted aralkylthio; substituted or unsubstituted amino; a carboxylic acid group; a carboxylic acid ester group; a carbocylic acid amide group; and a group having the formula —OC(O)$R^f$, where $R^f$ is selected from the group consisting of substituted or unsubstituted alkyl; substituted or unsubstituted aralkyl; substituted or unsubstituted aryl, a substituted or unsubstituted saturated, unsaturated, or aromatic heterocyclic group;

$R^{15}$ and $R^{16}$ are independently selected from the group consisting of hydroxy; substituted or unsubstituted alkoxy; substituted or unsubstituted arylxoxy; and substituted or unsubstituted aralkoxy; or $R^{15}$ and $R^{16}$, together, have the formula —O—Z—O— where Z is a substituted or unsubstituted alkylene moiety, and introducing an oxidizing agent to the compound under conditions effective to form the dioxatricyclodecane having two methyleneoxy bridges.

* * * * *